(12) United States Patent
Heeger et al.

(10) Patent No.: US 8,003,374 B2
(45) Date of Patent: *Aug. 23, 2011

(54) REAGENTLESS, REUSABLE, BIOELECTRONIC DETECTORS

(75) Inventors: Alan J. Heeger, Santa Barbara, CA (US); Chunhai Fan, Shanghai (CN); Kevin Plaxco, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 417 days.

This patent is subject to a terminal disclaimer.

(21) Appl. No.: 11/193,318

(22) Filed: Jul. 29, 2005

(65) Prior Publication Data

US 2007/0020641 A1 Jan. 25, 2007

Related U.S. Application Data

(63) Continuation-in-part of application No. 10/678,760, filed on Oct. 3, 2003, now abandoned, and a continuation-in-part of application No. 10/810,333, filed on Mar. 25, 2004, now abandoned.

(60) Provisional application No. 60/457,762, filed on Mar. 25, 2003.

(51) Int. Cl.
C12M 1/34 (2006.01)
C12M 3/00 (2006.01)
C12M 1/00 (2006.01)
C12Q 1/68 (2006.01)
C07H 21/04 (2006.01)

(52) U.S. Cl. ... 435/287.2; 435/6; 435/283.1; 435/287.1; 536/24.3

(58) Field of Classification Search ........... 435/6, 283.1, 435/287.1, 287.2; 536/24.3
See application file for complete search history.

(56) References Cited

U.S. PATENT DOCUMENTS

| | | | |
|---|---|---|---|
| 4,840,893 A | 6/1989 | Hill et al. | |
| 5,139,812 A | 8/1992 | Lebacq | 427/7 |
| 5,312,728 A | 5/1994 | Lizardi et al. | |
| 5,942,388 A | 8/1999 | Willner et al. | |
| 6,221,586 B1 | 4/2001 | Barton et al. | |
| 6,264,825 B1 | 7/2001 | Blackburn et al. | |
| 6,350,580 B1 | 2/2002 | Sorge | |
| 6,432,723 B1 | 8/2002 | Plaxico et al. | |
| 6,451,588 B1 | 9/2002 | Egholm et al. | |
| 2001/0024788 A1 | 9/2001 | Hashimoto | |
| 2002/0006617 A1 | 1/2002 | Fan et al. | |

(Continued)

FOREIGN PATENT DOCUMENTS

CN 1422960 6/2003

(Continued)

OTHER PUBLICATIONS

Drummond et al. Electrochemical DNA sensors. Nat Biotechnol 21:1192-1199 (2003).

(Continued)

*Primary Examiner* — Robert T. Crow
(74) *Attorney, Agent, or Firm* — Michael B. Rubin; Bozicevic, Field & Francis LLP

(57) ABSTRACT

A reagentless, reusable bioelectronic DNA, or other oligonucleotide sequence sensor is disclosed. The sensor includes an oligonucleotide (aptamer) probe tagged with a electroactive, redoxable moiety, self-assembled on or near an electrode. This surface-confined oligonucleotide (aptamer) probe structure undergoes hybridization-induced conformational change in the presence of the target which changes the electron-transfer distance between the redoxable moiety and the electrode thereby providing a detectable signal change. In an alternative embodiment, the target can harbor the redoxable moiety.

46 Claims, 15 Drawing Sheets

U.S. PATENT DOCUMENTS

| | | |
|---|---|---|
| 2002/0012930 A1 | 1/2002 | Rothberg et al. |
| 2004/0101890 A1 | 5/2004 | Meade et al. |
| 2004/0191801 A1 | 9/2004 | Heeger et al. |
| 2004/0219523 A1 | 11/2004 | Stanton et al. |
| 2005/0112605 A1 | 5/2005 | Heeger et al. |
| 2005/0233358 A1 | 10/2005 | Thorp et al. |
| 2007/0154909 A1 | 7/2007 | Xiao et al. |

FOREIGN PATENT DOCUMENTS

| | | |
|---|---|---|
| CN | 1422961 | 6/2003 |
| WO | WO/99/57317 | 11/1999 |
| WO | WO 01/40511 A2 | 6/2001 |
| WO | WO/2004/035829 | 4/2004 |
| WO | 2007120299 A2 | 10/2007 |

OTHER PUBLICATIONS

Immoos et al., Conformationally gated electrochemical gene detection.ChemBioChem 5:1100-1103 (2004).

Katz et al. Electroanalytical and Bioelectroanalytical Systems Based on Metal and Semiconductor Nanoparticles. J Electroanal 16:19-44 (2004).

Macaya et al. Structural and functional characterization of potent antithrombotic oligonucleotides possessing both quadruplex and duplex motifs. Biochemistry 34:4478-4492, 1995.

Padmanabhan,et al. An Ambiguous of a DNA 15-mer Thrombin Complex. Acta Crystallogr. D52:272-282 (1996).

Potyrailo et al. Adapting Selected Nucleic Acid Ligands (Aptamers) to Biosensors. Anal Chem 70:3419-3425 (1998).

Thorp et al. Cutting out the Middleman: DNA Biosensors Based on Electrochemical Oxidation. Trends Biotechnol 16:117-121 (1998).

Ihara et al "Ferrocene-oligonucleotide conjugates fro electrochemical probing of DNA" Nucleic Acids Res 24(21):4273-4280 (1996).

Yu, et al. Electronic Detection of Single-Base Mismatches in DNA with Ferrocene-Modified Probes: J. Am. Chem. Soc. 123:11155-11161 (2001).

Umek et al. "Electronic Detection of Nucleic Acids" J. Mol. Diag. 3(2):74-84 (2001).

Park et al. "Array-Based Electrical Detection of DNA with Nanoparticle Probes" Science 295:1503-1506 (2002).

Korri-Youssoufi, et al. "Toward Bioelectronics: Specific DNA Recognition Based on an Oligonucleotide-Functionalized Polypyrrole" J. Am. Chem. Soc. 119:7388-7389 (1997).

Clelland et al. "Hiding messages in DNA microdots" Nature 399:533-534 (1999).

Cox et al. "Bar coding objects with DNA" Analyst 126:545-547 (2001).

Fan et al. "Spectroscopy and Electrochemistry of the Covalent Pyridine-Cytochrome c Comples and a Pyridine-Induced, "Alkaline-like" Conformation" J. Phys. Chem. I(B) 106:11375-11383 (2002).

Hirst, J. et al. "Kinetics and Mechanism of Redox-Coupled, Long-Range Proton Transfer in an Iron-Sulfur Protein. Investigation by Fast-Scan Protein-Film Voltammetry" J. Am. Chem. Soc. 120:7085-7094 (1998).

Tyagi et al. "Molecular Beacons: Probes that Fluoresce upon Hybridization" Nat. Biotechnol. 14:303-308 (1996).

Boon et al. "An electrical probe of protein-DNA interactions on DNA-modified surfaces" Nat. Biotechnol. 20:282-286 (2002).

O'Sullivan, et al. "Aptasensors—the future of biosensing?" Anal. Bioanal. Chem. 372:44-48 (2002).

Robertson et al. "In vitro selection of an allosteric ribozyme that transduces analytes to amplicons" Nature Biotech 17:62-66 (1999).

Stojanovic et al. "Fluorescent Sensors Based on Aptamer Self-Assembly" J. Am. Chem. Soc. 122:11547-11548 (2000).

Cook et al. Methylated DNA labels for marking objects: Biotechnol. Lett 25:89-94 (2003).

Immoos et al. "Characterization of Immobilized DNA Hairpins Containing Tethered Redox Probes" Dept. of Chemistry, Duke University, P.M. Gross Laboratory, Durham, NC.

Brazill et al. "Sinusoidal voltammetry: a frequency based electrochemical detection technique" J. Electroanal Chem. 531:119-132 (2002).

Cheng et al. "Chip PCR. II. Investigation of different PCR amplification systems in microfabricated silicon-glass chips" Nuc. Acid. Res. 24(2):380-385 (1996).

Herne et al. "Characterization of DNA Probes Immobilized on Gold Surfaces" J. Am. Chem. Soc. 119:8916-8920 (1997).

Leopold et al. "Influence of Gold Topography on Carboxylic Acid Terminated Self-Assembled Monolayers" Langmuir 18:978-980 (2002).

O'Connor et al. "A Nernstian electron source model for the ac voltammetric response of a reversible surface redox reation using large-amplitude ac voltages" J. Electroanal. Chem. 466:197-202 (1999).

Ellington et al. "In vitro selection of RNA molecules that bind specific ligands" Nature 346:818-822 (1990).

Robertson et al. "Selection in vitro enzyme that specifically cleaves single-stranded DNA" Nature 344:467-469 (1990).

Bock et al. "Selection of single-stranded DNA molecules that bind and inhibit human thrombin" Nature 355:564-566 (1992).

Iqbal et al. "A review of molecular recognition technologies for detection of biological threat agents" Biosens. Bioelectron 15:549-578 (2000).

Tan et al. "Molecular beacons" Curr. Opin. Chem. Biol. 8:547-553 (2004).

Tombelli et al. "New Trends in Nucleic Acids Based Biosensors" Anal. Lett. 37(6):1037-1052 (2004).

Cox et al. "Automated Acquisition of Aptamer Sequences" Comb. Chem. & High Throughput Screening 5:289-299 (2002).

Li et al. "Molecular Adtamer Beacons for Real-Time Protein Recognition" Biochem. Biophys. Res. Commun. 292:31-40 (2002).

Hamaguchi et al. "Aptamer Beacons for the Direct Detection of Proteins" Anal. Biochem. 294:126-131 (2001).

Dittmer et al. A DNA-Based Machine That Can Cyclically Bind and Release Thrombin Agnew. Chem. Int. Ed. 43:3550-3549 (2004).

Pavlov et al. "Aptamer-Functionalized Au Nanoparticles for the Amplified Optical Detection of Thrombin" J. Am. Chem. Soc. 126:11768-11769 (2004).

Lee et al. "A Fiber-Optic Microarray Biosensor Using Aptamers as Receptors" Anal. Biochem. 282:142-146 (2000).

Minunni et al. "Development of biosensors with aptamers as biorecognition element: the case of HIBV-1 Tat protein" Biosens. Bioelectron. 20:1149-1156 (2004).

Fukusho et al. "In vitro selection and evaluation of rna aptamers that recognize arginine-rich-motif model peptide on a quartz-crystal microbalance" Chem. Commun. 1:88-89 (2002).

Liss et al. "An Aptamer-Based Quartz Crystal Protein Biosensor" Anal. Chem. 74(17):4488-4495 (2002).

Hianik et al. "Detection of aptamer-protein interactions using QCM and electrochemical indicator methods" Bioorg. Med. Chem. Lett. 15:291-295 (2005).

Rajendran et al. "In vitro selection of molecular beacons" Nucleic Acids. Res. 31(19):5700-5713 (2003).

Li et al. "Real-time Protein Monitoring Based on Molecular Beacons" Curr. Proteomics 1:315-324 (2004).

Fang et al. "Molecular Beacons" Cell. Biochem. Biophys. 37:71-81 (2002).

Stojanovic et al. "Aptamer-Based Folding Fluorescent Sensor for Cocaine" J. Am. Chem. Soc. 123:4928-4931 (2001).

Yamamoto et al. "Molecular beacon aptamer fluoresces in the presence of Tat protein of HIV-1" Genes Cells 5:389-396 (2000).

Savran et al. "Micromechanical Detection of Proteins Using Aptamer-Based Receptor Molecules" Anal. Chem. 76:3194-3198 (2004).

Fang et al. "Synthetic DNA Aptamers to Detect Protein Molecular Variants in a High-Throughput Fluorescence Quenching Assay" Chem Bio Chem 4:829-834 (2003).

Bowtell, D.L. "Options available—from start to finish—for obtaining expression data by microarray" Nat. Genet. 21:25-32 (1999).

Winzeler et al. "Fluorescence-Based Expression Monitoring Using Microarrays" Methods. Enzymol. 306:3-18 (1999).

Willner, Itamar "Biomaterials for Sensors, Fuel Cells, and Circuitry" Science 298:2407-2408 (2002).

Hianik et al. "The study of the binding of globular proteins to DNA using mass detection and electrochemical indicator methods" *J. Electroanal Chem* 564:19-24 (2004).

Fan et al. "Electrochemical interrogation of conformational changes as a reagentless method for the sequence-specific detection of DNA" *Proc. Natl. Acad. Sci. USA* 100:9134-9137 (2003).

Macaya et al. "Thrombin-binding DNA aptamer forms a unimolecular quadruplex structure in solution" *Proc. Natl. Acad. Sci. USA* 90:3745-3749 (1993).

Buijsman et al. "Design and Synthesis of a Possible Mimic of a Thrombin-Binding DNA Aptamer" *Bioorg. Med. Chem. Lett* 7:2027-2032 (1997).

Ho et al. "Optical Sensors Based on Hybrid Aptamer/Conjugated Polymer Complexes" *J. Am. Chem. Soc.* 126:1384-1387, 2004.

Padmanabhan et al. "The Structure of α-Thrombin Inhibited by a 15-Mer Singl-stranded DNA Aptamer" *Biol. Chem.* 268:17651-17654 (1993).

Smirnov et al. "Effect of Loop Sequences and Size on DNA Aptamer Stability" *Biochemistry* 39:1462-1468 (2000).

Kankia et al. Folding of the Thrombin Aptamer into a G-Quadruplex with $Sr^{2+}$:Stability, Heat, and Hydration *J. Am. Chem. Soc.* 123:10799-10804 (2001).

Wang et al. "A DNA Aptamer Which Binds to and Inhibits Thrombin Exhibits a New Structural Motif for DNA" *Biochemistry* 32:1899-1904 (1993).

Kuhr, et al. Electrochemical DNA analysis comes of age *Nature Biotech* 18:1042-1043 (2000).

Fritz, et al. "Electronic detection of DNA by its intrinsic molecular charge" *Proc. Natl. Acad. Sci.*, USA 99(22):4142-14146 (2002).

Brazill, et al. "Capillary Gel Electrophoresis with Sinusoidal Voltammetric Detection: A Stratego to Allow Four-"Color" DNA Sequencing" *Anal Chem.* 73:4882-4890 (2001).

Palecek, et al. "Electrochemistry of Nucleic Acids and Development of DNA Sensors" *Crit. Rev. Anal. Chem.* 32(3):261-270 (2002).

Millan et al. "Sequence-Selective Biosensor for DNA Based on Electroactive Hybridization Indicators" *Anal. Chem.* 65:2317-2323 (1993).

Kelley, et al. "Single-base mismatch detection based on charge transduction through DNA" *Nucleic Acids Res.* 27(24):4830-4837 (1999).

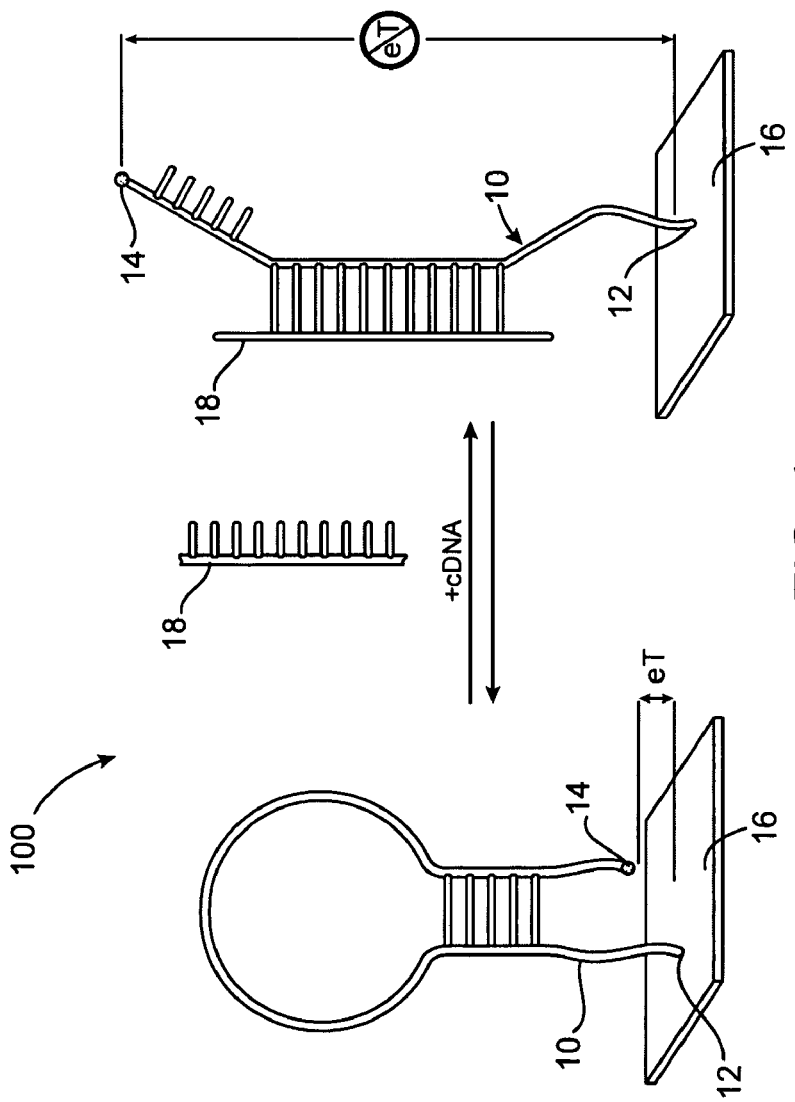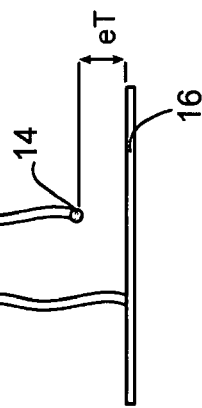

SEQUENCE LISTING

<160> NUMBER OF SEQ ID NOS: 8

<210> SEQ ID NO 1
<211> LENGTH: 27
<212> TYPE: DNA
<213> ORGANISM: Artificial
<220> FEATURE:
<223> OTHER INFORMATION: Synthetic oligonucleotide sequence
<220> FEATURE:
<221> NAME/KEY: misc_feature
<222> LOCATION: (1)..(1)
<223> OTHER INFORMATION: 5'-NH2-(CH2)6-G
<220> FEATURE:
<221> NAME/KEY: misc_feature
<222> LOCATION: (27)..(27)
<223> OTHER INFORMATION: C-(CH2)6-SH-3'

<400> SEQUENCE: 1
ncgaggtaaa acgacggcca gtctcgn                                       27

<210> SEQ ID NO 2
<211> LENGTH: 27
<212> TYPE: DNA
<213> ORGANISM: Artificial
<220> FEATURE:
<223> OTHER INFORMATION: Synthetic oligonucleotide

<400> SEQUENCE: 2
tttttactcg ccgtcgtttt actcttt                                       27

<210> SEQ ID NO 3
<211> LENGTH: 24
<212> TYPE: DNA
<213> ORGANISM: Artificial
<220> FEATURE:
<223> OTHER INFORMATION: Synthetic oligonucleotide

<400> SEQUENCE: 3
cgtatcattg gactggccat ttat                                          24

<210> SEQ ID NO 4
<211> LENGTH: 17
<212> TYPE: DNA
<213> ORGANISM: Artificial
<220> FEATURE:
<223> OTHER INFORMATION: Synthetic oligonucleotide

<400> SEQUENCE: 4

```
actggccgtc gttttac                                                    17
```

<210> SEQ ID NO 5
<211> LENGTH: 17
<212> TYPE: DNA
<213> ORGANISM: Artificial
<220> FEATURE:
<223> OTHER INFORMATION: Synthetic oligonucleotide

<400> SEQUENCE: 5

```
cgtatcattg gactggc                                                    17
```

<210> SEQ ID NO 6
<211> LENGTH: 31
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-HS-(CH2)6-T
<220> FEATURE:
<221> NAME/KEY: misc_feature
<222> LOCATION: (31)..(31)
<223> OTHER INFORMATION: T-(CH2)2-methylene blue-3'

<400> SEQUENCE: 6

```
naagttcatc tccccggttg gtgtggttgg n                                    31
```

<210> SEQ ID NO 7
<211> LENGTH: 27
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-HS-(CH2)6-G
<220> FEATURE:
<221> NAME/KEY: misc_feature
<222> LOCATION: (27)..(27)
<223> OTHER INFORMATION: C-(CH2)7-methylene blue-3'

<400> SEQUENCE: 7

```
ncgaggtaaa acgacggcca gtctcgn                                         27
```

<210> SEQ ID NO 8
<211> LENGTH: 31
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-HS-(CH2)6-T
<220> FEATURE:
<221> NAME/KEY: misc_feature
<222> LOCATION: (31)..(31)
<223> OTHER INFORMATION: T-(CH2)2-methylene blue-3'

<400> SEQUENCE: 8

```
naagttcatc tccccggtgg tggttgtggt n                                    31
```

REAGENTLESS, REUSABLE, BIOELECTRONIC DETECTORS

CROSS-REFERENCE TO RELATED PATENT APPLICATIONS

This application is related to and claims the benefit of U.S. Provisional Application Ser. No. 60/457,762 filed on Mar. 25, 2003 and U.S. Application Ser. No. 10/678,760 filed on Oct. 3, 2003 and is a C-I-P of U.S. application Ser. No. 10/810,333 filed on Mar. 25, 2004 (all incorporated by reference).

REFERENCE TO GOVERNMENT SUPPORT

This invention was made in part with government support under grants from the National Science Foundation (Grant No. NSF-DMR-0099843), the Office of Naval Research (Grant No. ONR N0014-1-1-0239) and the National Institutes of Health (Grant No. GM 62958-01 and Grant No. NIH EB002046).

BACKGROUND OF THE INVENTION

1. Field of the Invention

This invention relates to bioelectronic sensors and their use to detect hybridization events occurring in DNA, RNA, PNA and other oligonucleotide systems. In a preferred embodiment the detection of such hybridization events is used to detect and verify an oligonucleotide authentication tag. In another preferred embodiment the bioelectronic sensor incorporates an aptamer which undergoes a detectable change in the presence of a target for which the aptamer is specific.

2. Background Information

The detection of DNA, RNA, nucleic acids comprising base analogs, thiols, etc., and, to a lesser extent, PNA (hereinafter generally referred to as "oligonucleotides" and/or "polynucleotides") hybridization events is of significant scientific and technological importance, manifested in, for example, the rapidly growing interest in the chip-based characterization of gene expression patterns and the detection of pathogens in both clinical and civil defense settings [Heller, M. J., *Annu. Rev. Biomed. Eng.* 4, 129-153 (2002)]. Consequently, a variety of optical [Taton, T. A., Mirkin, C. A. & Letsinger, R. L. *Science* 289, 1757-1760 (2000); Gaylord, B. S., Heeger, A. J. & Bazan, G. C., *Proc. Nat. Acad. Sci. USA* 99, 10954 (2002); Cao, Y. W. C., Jin, R. C. & Mirkin, C. A., *Science* 297, 1536-1540 (2002)] and acoustic [Cooper, M. A. et al. *Nature Biotech.* 19, 833-837 (2001)] detection methods have been proposed.

In these assays one or more target oligonucleotides is brought into proximity to one or more oligonucleotide ligands and hybridization (if any) is detected by noting a change in a detectable "genosensor" moiety such as the presence of a suitable fluorolabel, radiolabel or enzyme label, present on the ligands.

Among these historic genosensors, fluorescence detection methods have historically dominated the state of the art [Heller, M. J., *Annu. Rev. Biomed. Eng.* 4, 129-153 (2002); Bowtell, D. D. L., *Nature Genet.* 21, 25-32 (1999); Winzeler, E. A., Schena, M. & Davis, R. W., *Methods Enzymol.* 306, 3 (1999)].

The application of electronic methods to the sensing of biologically related species has recently been attracting increased attention [Kuhr, W. G., *Nature Biotech.* 18, 1042-1043 (2000); Willner, I., *Science* 298, 2407 (2002); Fritz, J., Cooper, E. B., Gaudet, S., Sorger, P. K. & Manalis, S. R. Electronic detection of DNA by its intrinsic molecular charge. *Proc. Natl. Acad. Sci., U.S.A.* 99, 14142-14146 (2002)].

Advantages of bioelectronic detection include the following:

1. Electrochemical techniques offer the promise of sensitive, rapid and inexpensive screening [Bard, A. J. & Faulkner, L. R. *Electrochemical Methods* (John W. Willey & Sons, New York, 2001)].
2. Unlike fluorophores that quench or photo-bleach, typical electroactive labels are stable and relatively insensitive to their environment.
3. "Multi-color" labeling is possible by molecular design and synthesis that produce a "spectrum" of derivatives, each having a unique detectable electronic signal [Brazill, S. A., Kim, P. H. & Kuhr, W. G., *Anal. Chem.* 73, 4882-4890 (2001)].
4. The possibility of mass-production of bioelectronic detectors via the well-developed technical infrastructure of the microelectronics industry, renders electronic detection particularly compatible with microarray-based technologies.

Oligonucleotides are typically electrochemically silent at moderate applied voltages [Palecek, E. & Jelen, F., *Crit. Rev. Anal. Chem.* 32, 261-270 (2002)]. The first sequence-selective electronic method for DNA detection was based on the electrochemical interrogation of redox-active intercolators that bind preferentially to double-stranded DNA (dsDNA) [Millan, K. M. & Mikkelsen, S. R., *Anal. Chem.* 65, 2317-2323 (1993)]. More recently, the sensitivity of this detection approach was improved via electrocatalytic amplification [Kelley, S. O., Boon, E. M., Barton, J. K. & Jackson, N. M. H., *Nucleic Acids Res.* 27, 4830-4837 (1999)].

In an attempt to reduce high background deriving from the inappropriate binding of hybridization indicators to single-stranded DNA (ssDNA), a "sandwich" type detector has been developed. This approach utilizes an electrode-attached ssDNA sequence that binds the target to the electrode and a second, redox-labeled ligand sequence complimentary to an adjacent sequence on the target [Ihara, T., Maruo, Y., Takenaka, S. & Takagi, M., *Nucleic Acids Res.* 24, 4273-4280 (1996); Yu, C. J. et al., *J. Am. Chem. Soc.* 123, 11155-11161 (2001); Umek, R. M. et al., *J. Mol. Diag.* 3, 74-84 (2001)].

Mirkin and co-workers have developed an electronic DNA detection approach that has demonstrated high sensitivity and selectivity [Park, S. J., Taton, T. A. & Mirkin, C. A., *Science* 295, 1503-1506 (2002)]. In this resistance-based method, a probe-captured target undergoes a second hybridization event with Au nanoparticle-labeled DNA strands. Subsequent catalytic deposition of silver onto the Au nanoparticles leads to electrical contact and a detectable decrease in the resistance between electrode pairs as an indicator of hybridization.

Despite this interest in electronic oligonucleotide detection, there has been little progress toward the important goal of creating a sensor that is simultaneously sensitive, selective and reagentless (e.g., a sensor obviating further treatment with either hybridization indicators or signaling molecules to yield a detectable indication of hybridization). The "reagentless" feature has been reported in the context of a conjugated polymer-based electrochemical DNA sensor [Korri-Youssoufi, H., Garnier, F., Srivastava, P., Godillot, P. & Yassar, A., *J. Am. Chem. Soc.* 119, 7388-7389 (1997)]. However, this sensor has only moderate sensitivity due to broad, weakly-defined redox peaks.

More generally, while sensitivity of electronic oligonucleotide sensors of the prior art is impressive (ranging from 0.5 to 32 pM), no electronic sensors have been reported to meet the goal of fM sensitivity. The sensitive sensors require the addition of one or more exogenous reagents.

Recent, high profile examples ranging from geopolitical (e.g., forged documents purporting the solicitation of yellowcake sales to Iraq) to the medical (e.g. the recent recall of approximately 100,000 bottles of potentially counterfeit LIPITOR® (Atorvastatin Calcium) tablets) are indicative of the growing and increasingly complex risks associated with the counterfeiting of a wide range of documents and materials. Thus motivated, significant research has focused on the development of convenient-yet-unforgeable means of "authentifying" the provenance of documents, drugs and other materials related to medical, industrial, homeland or military security.

The use of DNA as an identifying label was first proposed by Philippe Labacq in U.S. Pat. No. 5,139,812 (issued Aug. 18, 1992). The approach works by concealing coded messages in DNA. Security is provided by the inherent sequence complexity of DNA (Clelland, C. T., Risca, V. and Bancroft, C. *Nature* 399, 533-534 (1999)).

Existing DNA-based authentication methods, however, have been limited to art, sports memorabilia and other high-value, low-volume applications. More widespread use of the approach has been limited by the cumbersome, time and reagent-intensive methods currently employed for the detection of low concentrations of a target DNA sequence in the presence of orders of magnitude larger background of masking DNA (Clelland, C. T., Risca, V. and Bancroft, C. *Nature* 399, 533-534 (1999); Cox, J. P. L. *Analyst* 126, 545-547 (2001)). Unfortunately, the technologies underlying counterfeiting generally keep pace with the technologies aimed at impeding such efforts. Thus, to date, no general, unbreakable means of "authenticating" documents, drugs and other high-volume materials has been reported.

It is the object of this invention to provide an electrochemical method for detecting specific sequences on target oligonucleotides, said method being simultaneously sensitive, selective, reagentless, and reusable. It is a further object to provide an electrochemical method for detecting an oligonucleotide-based (such as, for example, a DNA, RNA or peptide nucleic acid (PNA)-based) authentication tag.

It is a further object of this invention to provide aptamer-based bioelectronic sensors and to enable their use to detect aptamer-specific targets.

STATEMENT OF THE INVENTION

We have now discovered a detector and system for determining the presence of a target oligonucleotide having a target nucleotide sequence. The detector has an electrode capable of sensing redox events in a redoxable moiety and an immobilized oligonucleotide probe such as an aptamer designed to hybridize with a target nucleotide sequence or another target for which the oligonucleotide (aptamer) is specific. Either the probe (also referred to as the "sensor," "sensor element," or the like) or target (also referred to as the "tag," authentication tag," or the like) further comprises a redoxable moiety (also referred to a "redox moiety," "redox (able) chemical moiety," or the like).

In the case where the redoxable moiety is attached to the probe, such probe has a first configuration, in the absence of hybridization or other interaction with the target, which locates the redox moiety in a first position relative to the electrode. The probe has a second configuration in the presence of hybridization or other interaction with the target such as a target oligonucleotide, which locates the redox moiety in a second position relative to the electrode. The first and second positions give rise to distinguishable redox events that are detectable by the electrode.

The first position may be closer to the electrode than the second position or vice versa.

In presently preferred embodiments, the probe is immobilized on the electrode.

In some preferred embodiments one or both of the first and second configurations may include a stem and hairpin (stem and loop) configuration with the stem immobilized on the electrode and with the redox moiety attached to the end of the oligonucleotide probe distal from the stem.

In the case where the redoxable moiety is attached to the target oligonucleotide, the probe, in the absence of hybridization with the target oligonucleotide, produces only a background redox signal or produces no signal. A signal is produced only when the probe hybridizes with the target oligonucleotide harboring the redoxable moiety, thereby bringing the redoxable moiety in sufficiently close proximity to the electrode to produce a measurable signal.

In a second aspect, this invention concerns a method for detecting the presence of a target such as a target oligonucleotide having a target nucleotide sequence or other target in a sample. This method involves contacting the sample under oligonucleotide hybridization conditions or the like conditions to produce a specific interaction between the oligonucleotide (e.g. aptamer) on the detector and the target with the detector just described and sensing redox events in the redox moiety in the presence of the sample and redox events in the redox moiety in the absence of the sample and correlating similarity in redox events between the two sensings with the absence of the target and a change in redox events with the presence of the target.

In a third aspect this invention provides a rapid, reagent-less, E-DNA process for convenient, secure and inexpensive authentication. The E-DNA approach unambiguously determines the provenance of materials via the sequence specific detection of nanogram quantities of a oligonucleotide-based authentication tag. A many-fold excess of non-cognate, "masking oligonucleotides," which may be additionally present to thwart efforts to forge the authentication tag via cloning or sequencing, or may be present as a consequence of contamination or inherent in the materials to be authenticated, does not detectably alter the authentication signal. Using an inexpensive electrochemical workstation, robust authentication signals are obtained via, e.g., salt-water extraction of authentication tags from dried paper, dissolution of a solid forms of drugs, or from a sample of a liquid solution or suspension of a drug, all in about 10 minutes, and without further processing or the addition of exogenous reagents.

DETAILED DESCRIPTION OF THE INVENTION

Brief Description of the Drawings

This invention will be further described with reference being made to the drawings in which:

FIG. 1 is a not-to-scale, semi-perspective diagram illustrating the mechanism by which a detector of this invention provides an indication of an oligonucleotide hybridization event. In this embodiment, the detector provides a decrease in signal as a measure of hybridization. FIG. 1A is a not-to-scale, elevational side view of the diagrammatic depiction of the hybridization event shown in FIG. 1.

DESCRIPTION OF PREFERRED EMBODIMENTS

Representative E-DNA Sensors

Figure 2:
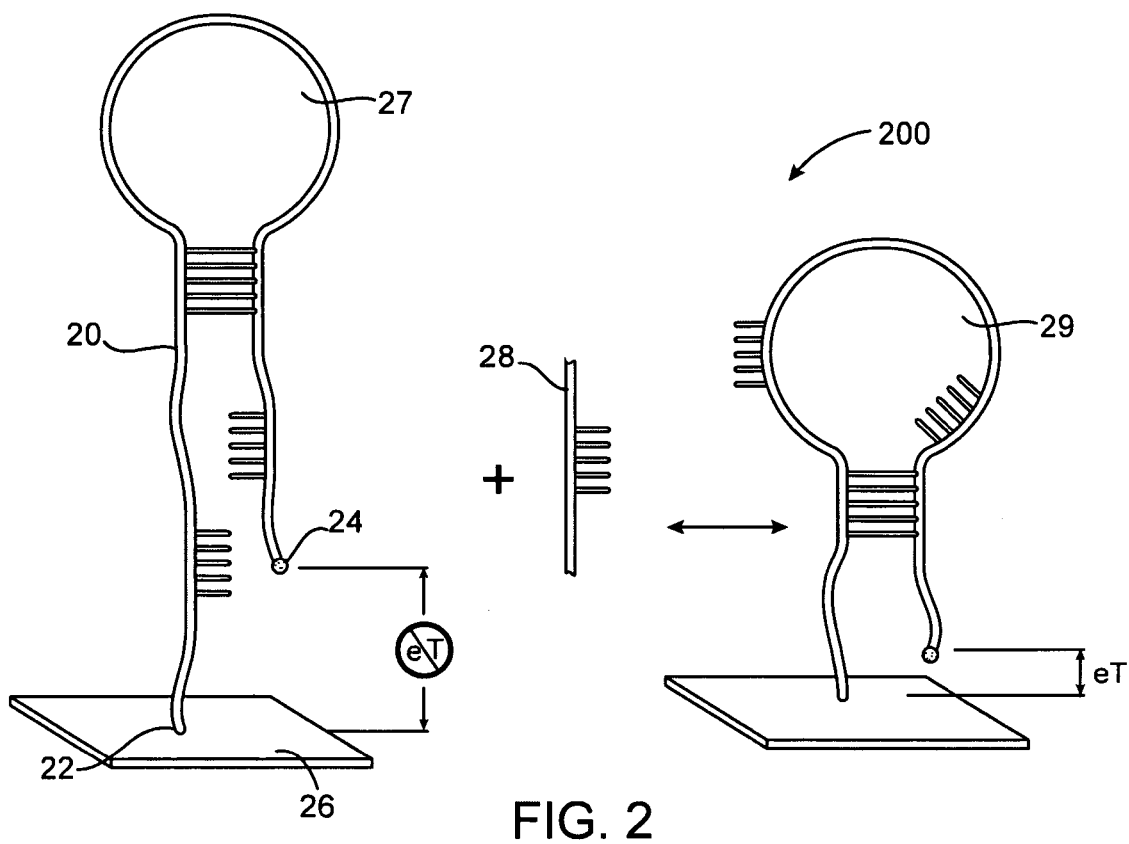
FIG. 2 is a second, not-to-scale diagram illustrating the mechanism by which a second embodiment of the detector of the invention provides an increase in signal as a measure of hybridization.

The present invention describes a reagentless, reusable method for detecting the presence and/or identity of oligonucleotides or polynucleotides using electronic sensors. The electronic sensors of the invention, which can be exquisitely sensitive, may be referred to herein as "E-DNA sensors."

As shown in FIG. 1, the E-DNA sensors can employ oligonucleotides capable of forming "stem-loop" or "hairpin" structures (also referred to "stem-loop" or "hairpin" DNA, or simply "stem-loops" or "hairpins"), with an electroactive label to detect hybridization events. Stem-loop DNA is an extremely interesting structure that forms the basis of the fluorescent, "molecular beacon" approach for homogeneous, optical hybridization detection [Tyagi, S and Kramer, F. R., *Nat. Biotechnol.* 14, 303-308 (1996)]. In stem-loop DNA, the base sequence is designed such that the structure is initially in the folded "hairpin" configuration. Formation of the hairpin structure is precluded, or disfavored in terms of assay equilibria, following hybridization with its specific complementary base sequences. The existence of the stem-loop structure in the design provides an on/off switch as well as a stringency test sufficient to discriminate single-base mismatches.

As used herein, different stem-loop or hairpin structures, such as those that exist in the presence or absence of a target oligonucleotide or polynucleotide, may be as referred to as "configurations".

"Target" refers to an oligonucleotide or polynucleotide having a sequence to which a particular electroactively-labeled oligonucleotide (also referred to as a "sensor" or "probe") is designed to hybridize. It can also refer to a small molecule of the like to which a particularly electroactivity—labeled oligonucleotide (also referred to as an "aptamer" or "labeled aptamer") is designed to hybridize.

The particular use of terms "oligonucleotide" and "polynucleotide" should in no way be considered limiting. "Oligonucleotide" is used when the relevant nucleic acid molecules typically comprise less than about 100 bases. "Polynucleotide" is used when the relevant nucleic acid molecules typically comprise more than about 100 bases. Both terms are used to denote DNA, RNA, modified or synthetic DNA or RNA (including but not limited to nucleic acids comprising synthetic and naturally-occurring base analogs, dideoxy or other sugars, and thiols), and PNA or other nucleobase containing polymers. However, probes and/or targets may comprise fewer than or more than 100 bases (inclusive). Accordingly, the terms "oligonucleotide" and "polynucleotide" are used to describe particular embodiments of the invention. The terms in no way define or limit the length of the nucleic acids that may be used to practice the invention.

In sensor 100 of FIG. 1, a hairpin oligonucleotide 10 possessing, for example, a thiol 12 and a redoxable chemical moiety 14 such as, for example, a ferrocene group or a methylene blue group, is immobilized on a gold electrode 16 via self-assembly. In the "closed state," oligonucleotide 10 presents a stem-loop structure that localizes the redoxable chemical moiety 14 in close proximity to the gold surface 16. Thus the distance between the gold and redoxable chemical moiety is sufficiently short for facile electron transduction (eT), thereby enabling redox of the redoxable chemical moiety in response to potentials applied via electrode 16. In the "open state," following hybridization with a complementary oligonucleotide 18, electron transfer between the redoxable chemical moiety 14 and the electrode 16 is blocked since moiety 14 is separated from the electrode surface. The distance for which eT is or is not facile is clearly illustrated in FIG. 1A, which corresponds to FIG. 1 but is drawn in side view, as opposed to FIG. 1, which is in semi-perspective view.

In the embodiment 100 described in FIG. 1, the E-DNA sensor suffers from being a "signal-off" sensor. That is, in response to its target, the electrochemical signal is abolished. This renders that embodiment of the E-DNA detector vulnerable to false positives arising via disruption of the stem-loop sensor element by environmental conditions or physical degradation (e.g. by nucleases). As shown in FIG. 2, with the appropriate oligonucleotide design, a "signal-on" E-DNA sensor 200 can be engineered, thus silencing false positives arising due to chemical or enzymatic destruction of the sensor element. The appropriate structure contains an oligonucleotide probe 20 attached to or adjacent to electrode 26 at end 22. The other end of probe 20 carriers a redoxable moiety 24. In one configuration, probe 20 contains a moderate length hairpin 27 that positions the electroactive label 24 away from the electrode 26. That hairpin configuration 27 thermodynamically competes with a less stable hairpin configuration 29. The less stable hairpin 29 positions the label 24 in proximity to the electrode 26. Hybridization with target 28 disrupts and/or destabilizes hairpin structure 27, favoring the formation of hairpin structure 29, which brings the label 24 into proximity with the electrode 26, resulting in a signal.

Figure 3:
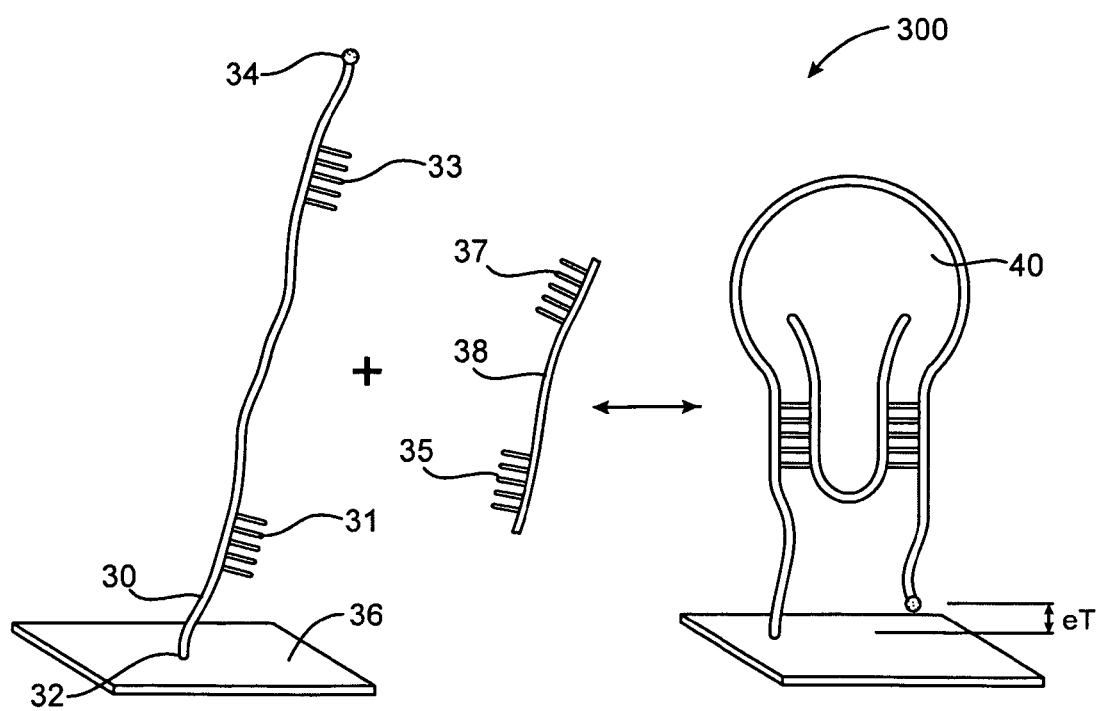
FIG. 3 is a third, not-to-scale diagram illustrating a third mechanism by which a third embodiment of the detector of the invention provides an indication of hybridization.

In another embodiment, as shown in FIG. 3, an oligonucleotide probe 30 may be coupled near or to electrode 36 via bond 32. The end of probe 30 distant from the point of attachment 32 is labeled with redoxable moiety 34. In the absence of target 38, probe 30 is "open" and label 34 is a long distance from electrode 36. In this embodiment, probe 30 contains regions 31 and 33 which are complementary to regions 35 and 37 on target 38. When target 38 and probe 30 are hybridized or otherwise specifically interact, target 38 bridges regions 31 and 33 of probe 30 to form loop 40, and thus positions redoxable moiety 34 in sufficient proximity to electrode 36 to promote electron transduction, which can be detected.

Figure 4:
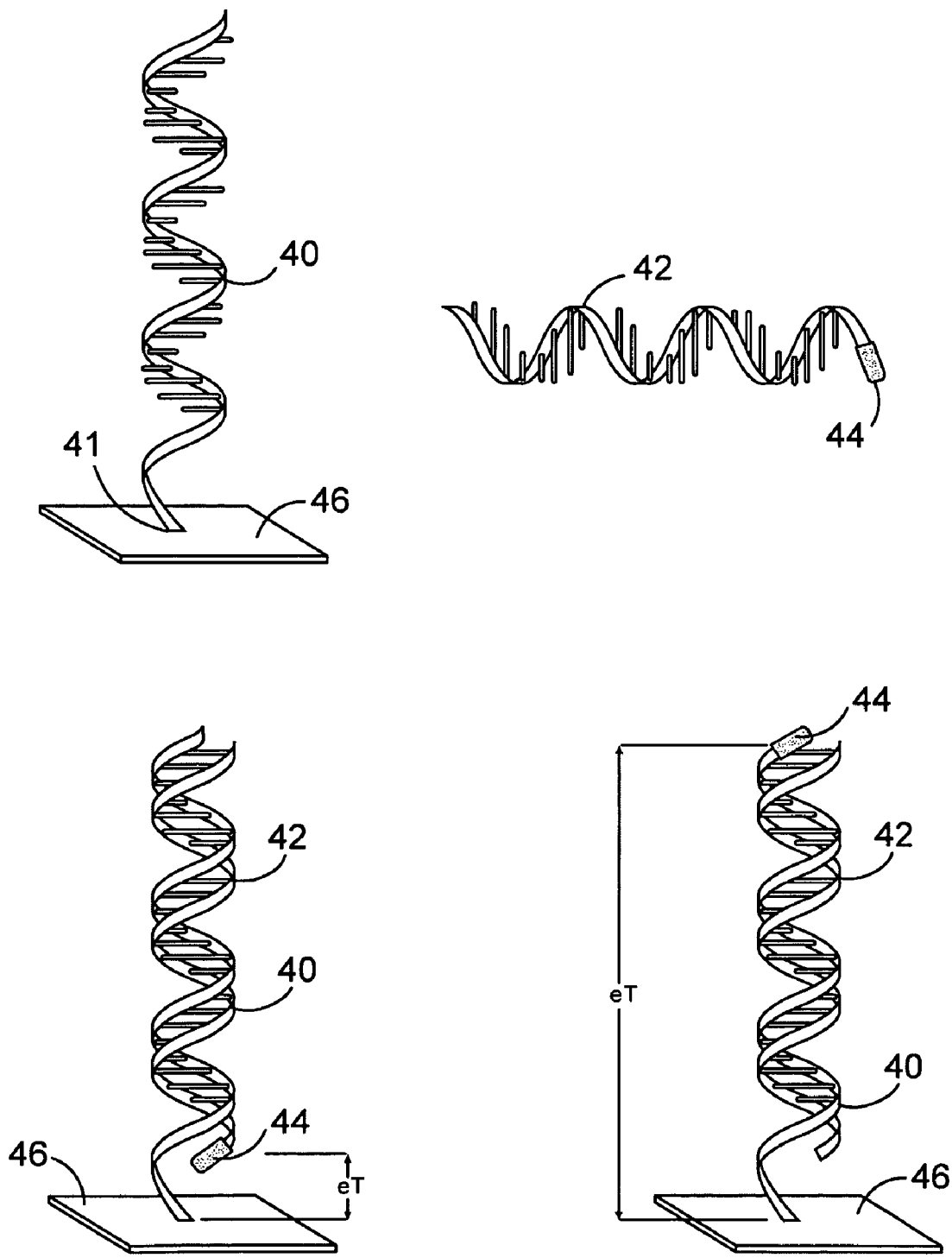
FIG. 4 is a fourth, not-to-scale diagram illustrating two additional mechanisms by which additional embodiments of the detector of the invention provides an indication of hybridization.

As shown in FIG. 4, one can also achieve a signal based on hybridization in systems not involving stem-loop or hairpin structures. In FIG. 4, an oligonucleotide 40 possessing a terminal thiol group or other suitable binding group is immobilized at a gold electrode 46 via bond 41. A target 42 bearing redoxable label 44 is brought into proximity to the bound oligonucleotide 40. In the absence of target there is no signal. Upon hybridization with the target, the label is brought into sufficient proximity to the electrode to allow electron transfer (eT), producing a measurable electrochemical signal.

In this embodiment, the hybridization system of the invention utilizes an electrochemical approach with a "signal-on" feature to identify oligonucleotide tags. The strategy demonstrated in FIG. 4 involves a gold electrode 46 and a DNA probe strand 40 without electroactive labels. The probe 40 sequence is designed to be complementary to the target oligonucleotide or polynucleotide 42 (e.g., an authentication tag present in a material to be authenticated) and contains a 5' thiol. The probe is assembled on the gold surface through gold-thiol chemistry. The target 42 additionally comprises methylene blue as the electroactive label 44 at either its 5' end, its 3' end, or both. The target may be encapsulated or otherwise secreted in documents or drugs. Prior to detection, the gold electrode has no signal since it has only the probe DNA without a redoxable moiety. After hybridization with target oligonucleotides (e.g., eluted from material to be authenticated) the label is brought to the electrode surface and creates the electrochemical signal. The "signal-on" process is due to either the direct electron tunneling into the redox molecule from the gold electrode (left image), or through electron transfer mediated by the hybridized DNA (right image) (Boon, E. M., Salas, J. E. and Barton, J. K., Nat *Biotechnol.* 20, 282-286 (2002)). Since the signal is created only after hybridization, this approach offers the advantage of being insensitive to environmental contaminants.

These are but four representative configurations for the E-DNA sensor. Any probe configuration which will present different configurations in the presence and absence of target DNA, and that can reposition a redox label in electrically distinguishable different proximities to the sensing electrode can be used.

Representative Materials

In the embodiments just described, the redoxable chemical moiety has been ferrocene or methylene blue. More generally, any redoxable chemical moiety that is stable under assay conditions can be used. Examples include, but are not limited to, purely organic redox labels, such as viologen, anthraquinone, ethidium bromide, daunomycin, methylene blue, and their derivatives, organo-metallic redox labels, such as ferrocene, ruthenium, bis-pyridine, tris-pyridine, bis-imidizole, and their derivatives, and biological redox labels, such as cytochrome c, plastocyanin, and cytochrome c'.

In a preferred embodiment, the electrode is fabricated from known electrode materials such as, for example, gold, silver, platinum, carbon, or silicon. Gold gives good results.

In a preferred embodiment, the surface of the electrode is functionalized with the oligonucleotide probe structure through self-assembly, such as through the well-established gold-S chemistry of self assembly.

It is also preferred that when the electrode surface, functionalized with the oligonucleotide probe structure, is subsequently passivated by materials such as 2-mercaptoethanol, (2-ME), 6-mercaptohexanol or mercaptoalkanols generally ($HS-(CH_2)_n-OH$ with n=2~18) and the like.

Ideally, the stem-loop oligonucleotide structures are loosely packed on the gold surface in order to minimize steric effects that could interfere with hybridization.

Preferred embodiments for stem-loop structure are well known in the art. For example, the stem-loop structure may be designed such that about five bases at a relative 5'-end and relative 3'-end are fully complementary. The base sequence in the loop region of the stem loop DNA may be selected so as to be complementary to the specific base sequence to be detected in the target DNA. In addition, the use of complementary G-C rich sequences may be desirable to enhance "stem" stability in stem-loop structures.

In some embodiments, the probe structure comprises an oligomer of neutral peptide nucleic acid (PNA) in place of the DNA oligonucleotide to allow hybridization to occur at ambient ionic strengths. In addition to silencing and detecting false positives, degradation of the sensor element can be avoided by building the stem-loop element from peptide nucleic acid (PNA). PNA is chemically and enzymatically robust and, because it is uncharged, forms stronger duplexes with DNA or RNA than ssDNA. Thus, there are clear advantages to "E-DNA" sensors comprising synthesized PNA sensor elements.

The oligonucleotide probe may be attached to the electrode via a "molecular-wire" such as, for example, an oligo(phenylene vinylene) in order to facilitate electron transfer.

The sensor can also employ aptamers. An aspect of the E-DNA detection is the electrochemical detection of a target-induced conformational change. This means that this invention may be generalizable to other types of tags and analytes where conformational change occurs upon binding, such as protein folding or aptamer folding based biosensors.

Aptamers are DNA or RNA molecules that adopt well-defined tertiary structures analogous to natural enzymes. Aptamers have emerged as promising therapeutic and diagnostic tools [Chang, K. Y. & Varani, G., Nature Struct. Biol. 4, 854-858 (1997); Burgstaller, P., Girod, A. & Blind, M., Drug Discov. Today 7, 1221-1228 (2002); Wilson, D. S. & Szostak, J. W., Annu. Rev. Biochem. 68, 611-647 (1999)]. Well-developed in vitro selection methods have been able to produce aptamers for virtually any target [Wilson, D. S. & Szostak, J. W., Annu. Rev. Biochem. 68, 611-647 (1999); Griffiths, A. D. & Tawfik, D. S., Curr. Opini. Biotech. 11, 338-353 (2000)]. Given these advantages, oligonucleotide aptamers are anticipated to play an important role in next-generation biosensing elements [Sullivan, C. K. O., Anal. Bioanal. Chem. 372, 44-48 (2002); Robertson, M. P. & Ellington, A., Nature Biotech. 17, 62-66 (1999)].

DNA or RNA aptamers that undergo significant conformational changes upon binding specific analytes are readily available. In vitro selection techniques are able to isolate highly affinitive RNA or DNA aptamers that bind almost any arbitrary small molecule, biomacromolecule or cell type. Many aptamers undergo significant conformational changes upon analyte binding. Alternatively, although insignificant signal changes are expected for aptamers that undergo subtle conformational changes, it is feasible to accomplish analyte detection via combining a recently proposed aptamer self-assembly approach [Stojanovic, M. N., de Prada, P. & Landry, D. W., J. Am. Chem. Soc. 122, 11547-11548 (2000)]. For example, aptamers rationally dissected into two halves, with one immobilized at electrode surfaces and the other tagged with electroactive label, are expected to be split in the absence of analytes while self-assembled upon analyte binding. Thus the approach described here can be generalized from stem-loop structures to DNA and RNA aptamers and thereby to sensing platforms directed against essentially any water soluble analyte.

Reaction Conditions and Detection Methods

The hybridization events that are sensed by the detectors, and methods of this invention, are carried out in aqueous liquid environment. Aqueous environments are preferable but optionally rendered at least somewhat ionic by the presence of dissolved salt. It is generally understood that ionic environments favor hybridization. "Salt" is defined to include sodium chloride but also any other water-soluble alkaline earth or alkyl metal ionic materials. Magnesium, potassium, calcium, and/or manganese salts may be particularly useful for practicing the invention. While there may be advantages to particular salt materials or levels, they are not seen to be critical to the practice of this invention. Representative salt levels can be as high as about 4 or 5 molar, in some cases and as low as nearly zero. In the examples, 1 molar NaCl is generally used. Thus, salt levels of from about 0.05 to about 2 molar are presently preferred. In a particular embodiment of the invention, a physiological salt concentration (i.e., about 150 mM) is used. In other embodiments of the invention, the salt concentrations may bracket physiological salt conditions, e.g., from about 75 mM to about 300 mM.

Hybridization can be carried out in the presence of agents and additives that promote the desired hybridization, diminish nonspecific background interactions, inhibit the growth of microorganisms, or increase the stability of the probe and/or target oligonucleotides. For example, one can add up to 10% by weight or volume (based on the amount of aqueous environment) and particularly from about 1 or 2% to about 10% of one or more polyols. Representative polyols include glycerol, ethylene glycol propylene glycol sugars such as sucrose or glucose, and the like. One can also add similar levels of water soluble or water dispersible polymers such as polyethylene glycol (PEG) or polyvinyl alcohol or the like. Another representative additive is up to about 1 or 2% by weight (again based on the liquid substrate) of one or more surfactants such as triton X-100 or sodium dodecyl sulfate (SDS). All of these agents are electrochemically silent at the potentials observed with the sensors and methods of the invention. As a comparison of the results shown in FIG. 11 with the results shown in FIG. 10 make clear, the use of certain additives can lead to dramatic improvements in signal. A variety of hybridization conditions have been described and are well known in the art. Many such hybridization conditions are useful for practicing the invention.

Hybridization can be carried out at ambient temperature, although any temperature in the range over which hybridization is stable can be used. A preferred range is from about 5 to about 45° C. Hybridization times should be a short as possible for convenience. Times as short as minutes (e.g., about 1 to 5 minutes) can be used. Times of up to 5, 10, 15, 20, 30, 45, or 60 minutes, or longer may also be used. We have had good results with hybridization times of from about 15 to about 45 minutes. Hybridization temperatures and times may be determined empirically or using, e.g., CoT analysis or other methods of predicting hybridization conditions.

Multiplexing

False positives can be identified via multiplexing, e.g., using multiple, electrochemically distinct labels, such that the sensor and one or more control elements are integrated into a single sensor pixel. By employing multiple labels with narrow, non-overlapping redox potentials, 2-5 or possible more distinct sequences can be simultaneously interrogated on a single electrode. This enables the inclusion of internal controls, i.e., elements that are not complementary to known sequences that would respond to false positives arising due to non-specific disruption or degradation of the stem-loop. Multiplexing will also facilitate signal redundancy, alleviating the risk of masking in the unlikely event of contaminants with redox potentials precisely where the primary label reports. In addition to exhibiting narrow, non-overlapping redox peaks, the appropriate labels for multiplexing should be stable and synthetically facile. Electroactive labels that meet these requirements, include a large number of ferrocene [Brazill, S. A., Kim, P. H. & Kuhr, W. G., *Anal. Chem.* 73, 4882-4890 (2001)] and viologen derivatives (Fan, C., Hirasa, T., Plaxco, K. W. and Heeger, A. J. (2003)) *Langmuir*, and any redoxable species, such as methylene blue, anthraquinone, ethidium bromide, daunomycin.

Improving Sensitivity

AC voltammetric methods are commonly employed in an effort to delineate between redox and charging currents based on the different timescales for the two processes. Double-layer formation is limited only by ion mobility and thus equilibrates rapidly, whereas redox currents are limited by Marcus-type barriers and is orders of magnitude slower. Sinusoidal voltammetry (SV) or pulsed voltammetry has proven particularly useful; in addition to the SV frequency spectrum, time course data is obtained at each harmonic frequency element by performing the digital equivalent of a lock-in amplifier (Brazill S A, Bender S E, Hebert N E, et al. *J. Electroanal. Chem.*, 531, 119-132 (2002)). That is, the instantaneous current is monitored at the optimum phase angle for the signal of interest, thus greatly increasing the sensitivity and selectivity over traditional voltammetric techniques. This temporal deconvolution enables a large increase in peak to charging current ratios and thus an improvement in the E-DNA sensitivity by orders of magnitude. Cyclic voltammetry is also used.

Improving Peak Currents

The use of multiple redoxable chemical moieties will significantly increase the sensitivity. A straightforward approach to this end would be to label the single sensor strand with multiple redoxable chemical moieties. The sensor oligonucleotide element in FIG. 1 is modified on the 2' position of the terminal nucleotide, but modification of internal nucleotides is equally facile and should not significantly reduce the stability of the stem element. Because the electroactive label is isolated from the nucleotide, e.g., by a pentyl linker, the labels will not interact with one another and thus multi-labeled sensor elements will exhibit redox peaks at the same potential (and peak width) as single-labeled probes. Because peak current is proportional to the number of electron acceptors/donors this approach will only improve peak currents by a factor of 2-5, with the upper limit corresponding to the number of electron acceptors that can be packed onto the about 5 bases in the terminal stem sequence.

Electrocatalysis, in contrast, provides a potential means of increasing peak currents by orders of magnitude. The approach works by the addition of an electrochemical mediator, such as ferrocyanide, that is not reduced by the electrode but can be reduced by the ferrocene label (Boon, E. M., Ceres, D. M., Drummond, T. G., Hill, M. G., Barton, J. K. *Nat. Biotech.*, 18, 1096-1100 (2000)). Thus, in the presence of ferrocyanide, the electrode repeatedly reduces each ferrocene, thus catalytically increasing peak currents. This approach leads to a sensor that is no longer reagentless.

Tag Detection and Authentication

This invention provides a reagentless, electronic means for rapidly, specifically and inexpensively detecting DNA-based authentication tags, optionally in the presence of security-relevant levels of masking DNA (discussed in more detail, below). The method is suitable for the authentication of a wide range of items, including but not limited to, documents, medications (e.g., ingested, inhaled, injected, and/or topical pharmaceutical agents), food, and any physical objects in or upon which an oligonucleotide can be associated for the purpose of later authentication.

With this E-DNA sensor and optionally alternating current voltammetry (ACV), it is possible to produce a read-out of information encoded in an oligonucleotide, whether it be on packaging or on a label or the like or deposited on or dispersed in a solid or liquid. Only a small amount of oligonucleotide (e.g., about 5 ng for paper and about 20 ng for drugs) is necessary for detection as an authentication tag. More importantly, the E-DNA sensor can discriminate against a great excess of non-cognate oligonucleotide, which acts as a mask in order to thwart efforts to forge the authentication tag via cloning or sequencing.

Accordingly, oligonucleotides the E-DNA sensor conveniently identifies the hidden oligonucleotide sequence information in minutes. Given the simplicity and usefulness of this novel technology, it finds application in a variety of markets.

The one or more oligonucleotide authentication tags that will take part in the hybridization to a probe sequence may be mixed with a multi-fold concentration, such as 50 fold to 500,000 fold, e.g. 10,000 fold of non-cognate, masking oligonucleotide, and used in document and drug authentication and the like.

In this application, the oligonucleotide solution containing both authentication tag and masking oligonucleotide may be deposited on a piece of paper or similar carrier material. The paper is dried and associated with (e.g., attached to or the like) to the object to be authenticated. In the authentication stage, the paper is immersed in, for example, salt water to elute the tag. The eluted tag is ready for E-DNA detection.

In similar embodiments, oligonucleotide tags may be admixed in a solid, for example, a solid drug such as LIPITOR® (Atorvastatin Calcium) powder, and thereafter dispersed in salt water and tested by the E-DNA sensor.

The E-DNA authentication strategy is particularly refractory to counterfeiting. The extremely high selectivity of the E-DNA sensor enables us to specifically detect the authentication oligonucleotide sequence even in the presence of up to about a 10,000-fold, or even greater, excess of non-cognate "masking" oligonucleotide. Representative masking levels can be a three-fold or greater excess, preferably a ten-fold or greater excess, and especially a 50-fold or greater excess. This high level of masking would render it extremely difficult to forge the authentication tag via cloning or other amplification, sequencing and/or copying methods. Moreover, the E-DNA approach is also suitable for the detection of peptide nucleic acid (PNA)-based authentication tags. Because PNA cannot be amplified or sequenced via enzymatic methods the use of such tags would render the approach still more refractory to copying-based counterfeiting.

As described, the E-DNA approach could potentially be partially circumvented via dilution, i.e., the extraction and dilution of the authentication tag from one document and its application to several forged documents, or via the inclusion of materials (denaturants, nucleases, etc.) that would disrupt or overwhelm stem hybridization. Attacks based on the former, however, can be frustrated via measurements of the absolute oligonucleotide concentration in the authentication sample and ratiometric measurements of the absolute oligonucleotide content versus the concentration of authentication tag. Methods of quantitating nucleic acids are well-known in the art. Similarly, the latter circumvention can be thwarted by ratiometric measurements of authentication tag versus control sequences known to be absent in authentic goods. Given that the small electrode size and reagentless nature of the E-DNA sensor renders it particularly well suited for dense, electronic sensor arrays, such radiometric measurements do not present a significant hurdle.

Microelectrodes and Arrays

Because E-DNA involves an electronic sensor (e.g., a redoxable moiety), advances in electrophoretically-improved hybridization times can be applied [Cheng, J., Shoffner, M. A., Hvichia, G. E., Kricka, L. J., Wilding, P. (1996). *Nuc. Acid Res.*, 22, 380-385; Cheng, J., Sheldon, E. L., Wu. L., Uribe, A., Gerrue L. O, Heller, M. O'Connell, J. (1998). *Nat. Biotech.* 16, 541-546]. Moreover, because of its direct integration into electronics and excellent scalability (in the Example 1, 2 $mm^2$ electrodes were used, but E-DNA's impressive signal strength suggests that significantly smaller electrodes can be employed), E-DNA is well suited for applications in electronic gene detection arrays. To this end, biomaterials can be deposited onto specific pixels of gold "nanode" arrays and electrochemically addressed.

In a more preferred embodiment, the microelectrodes are arrayed in the format of N "pixels" with each pixel containing a unique stem-loop or the like oligonucleotide structure and with all microelectrodes electrochemically addressable, thereby enabling detection of N different targets.

As demonstrated in the following examples, the bioelectronic sensor described herein is both sensitive and highly selective. The sensitivity and selectivity of the E-DNA sensor is better than that of typical CCD-based fluorescent detectors, and is comparable to a recently proposed, conjugated polymer-based fluorescence amplification method [Gaylord, B. S., Heeger, A. J. and Bazan, G. C., *Proc. Nat. Acad. Sci. U.S.A.* 99, 10954 (2002); Moon, J. H., Deans, R., Krueger, E. and Hancock, L. F., *Chem. Commun.*, 104-105 (2003)]. The key sensing element, e.g., an oligonucleotide associated with a rexobale moiety, is compatible with normal solid-state synthesis of oligonucleotides. Moreover, the surface assembly process is robust and facile. Since the entire set-up can be conveniently prepared and is generally compatible with chip-based technology, the novel, reagentless detection described here provides a promising alternative to fluorescence-based sensors for most if not all of their applications.

The following general methods and specific examples are presented to illustrate the invention and are not to be considered as limitations thereon.

EXAMPLES

Example 1

Fabrication of the Stem-loop DNA Structure

Ferrocene carboxylic acid was purchased from Aldrich (Milwaukee, Wis.), 1-Ethyl-3-(3-dimethylaminopropyl)-carbodiimide (EDC) and N-hydroxysuccinimide ester (NHS) were obtained from Sigma (Milwaukee, Wis.). Ferrocene succinimide ester (Fc-NHS) was prepared as described in the literature [Takenaka, S., Uto, Y., Kondo, H., Ihara, T. & Takagi, M. *Anal. Biochem.* 218, 436 (1994)] and confirmed by $^1H$ NMR. Oligonucleotides were obtained from Synthegen (Houston Tex.). The sensor oligonucleotide, sequence 5'-$NH_2$—$(CH_2)_6$-GCGAG GTA AAA CGA CGG CCA GT CTCGC-$(CH_2)_6$—SH-3' (SEQ ID NO: 1) (oligo 1), contained a 5' hexamethylene amine and a 3' hexamethylene thiol group. Fc-NHS was dissolved in a small volume of dimethyl sulfoxide and then diluted in a 0.1 M $Na_2CO_3$ buffer (pH 8.5) containing 0.1 mM of oligo 1. This mixture was stirred overnight at room temperature. The final product (oligo 1-Fc) was purified by HPLC on a C18 column and confirmed by electrospray mass spectroscopy. The sequences of the target and control DNA oligos were 5'-ttttt ACT GGC CGT CGT TTT AC tcttt-3'(SEQ ID NO: 2) and 5'-CGT ATC ATT GGA CTG GCC ATT TAT-3' (SEQ ID NO: 3). All solutions were prepared with nano-pure water.

Example 2

Preparation of the Functionalized Au Electrode

Polycrystalline gold disks (1.6 mm diameter; BAS Inc., West Lafayette, Ind.) were used as working electrodes. The protocol for gold electrode preparation has been previously described [Fan, C., Gillespie, B., Wang, G., Heeger, A. J. & Plaxco, K. W., *J. Phys. Chem.* (B) 106, 11375-11383 (2002)]. The cleaned gold electrode was rinsed, dried under argon and then immediately incubated overnight in 1 M oligo 1-Fc, 10 mM phosphate buffer with 0.1 M NaCl, pH 7.4. Prior to use, the oligo 1-Fc was pre-treated with tris-(2-carboxyethyl) phosphine to break disulfide bonds and then purified using a spin column. The modified electrode was washed with water, dried under argon and incubated in 1 M $NaClO_4$ solution prior to use.

The gold surface was then functionalized by oligo 1 (see Example 1) through the well-established gold-S chemistry of self-assembly. Previous studies have demonstrated that this self-assembly process is only feasible in the presence of salt; in that high ionic strength leads to high surface density and closely packed DNA strands while low ionic strength produces loosely packed DNA strands [Boon, E. M., Salas, J. E. & Barton, J. K., *Nature Biotech.* 20, 282-286 (2002)]. For this Example, a relatively low ionic strength (0.1 M NaCl) was chosen to produce a loosely packed surface in order to minimize steric effects that could interfere with reversible hairpin formation (see FIG. 1). The prepared surface was subsequently passivated by 2-mercaptoethanol (2-ME). This process has been reported to "cure" the relatively disordered self-assembled monolayer (SAM) by gradually displacing nonspecifically adsorbed oligonucleotides [Herne, T. M. & Tarlov, M. J., *J. Am. Chem. Soc.* 119, 8916-8920 (1997)]. This oligonucleotide-containing, passivated surface has proven to be resistant to random DNA sequences, as reported previously [Herne, T. M. & Tarlov, M. J., *J. Am. Chem. Soc.* 119, 8916-8920 (1997)] and independently confirmed in our labs by monitoring with a quartz crystal microbalance.

Example 3

Characterization of the E-DNA Modified Electrode

The stem-loop structure localizes the ferrocene tag in close proximity to the gold surface (see Example 2 and FIG. 1) and thereby ensures that the distance between the gold electrode and the ferrocene moiety is sufficiently short to promote electron transfer.

Cyclic Voltammetry (CV) was performed using a CHI 603 workstation (CH Instruments) combined with a BAS C-3 stand. A platinum electrode was used as a pseudo-reference electrode while potentials are reported versus the normal hydrogen electrode (NHE). Background subtraction was conducted in some cases using Origin 6.0 (Microcal Software, Inc.) in order to remove non-Faradayic currents and improve signal clarity [Fan, C., Gillespie, B., Wang, G., Heeger, A. J. & Plaxco, K. W., *J. Phys. Chem.* (B) 106, 11375-11383 (2002); Hirst, J. et al. *J. Am. Chem. Soc.* 120, 7085-7094 (1998). Bard, A. J. & Faulkner, L. R. *Electrochemical Methods* (John W. Willey & Sons, New York, 2001)]. All experiments were conducted at room temperature.

Figure 5A:
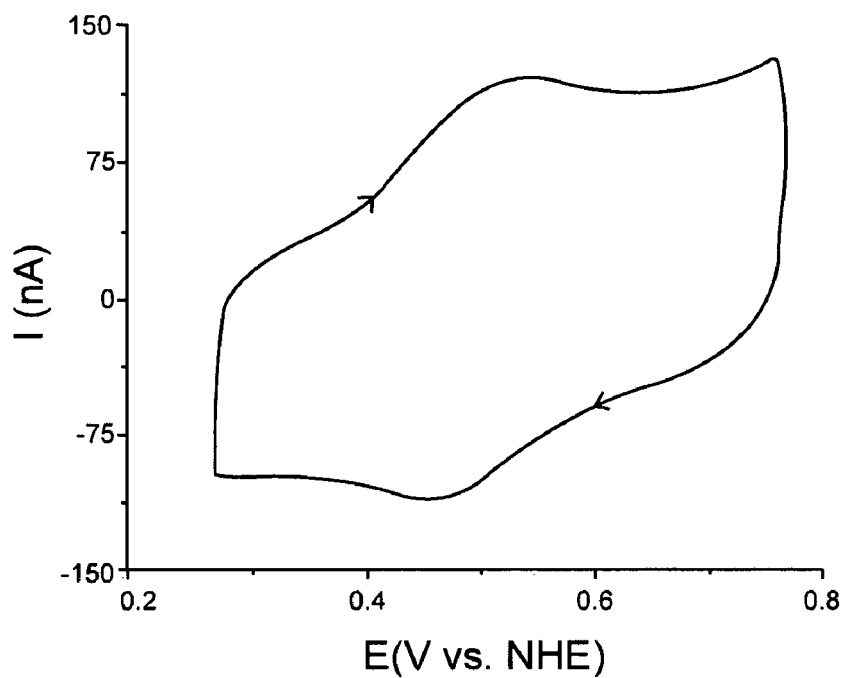
FIG. 5A is a cyclic voltammogram for a gold electrode modified with the ferrocene tagged, stem-loop-forming oligonucleotide in a 1 M $NaClO_4$ solution, at a scan rate of 0.1 V/s.

In the absence of target DNA, ferrocene redox peaks were observed (FIG. 5a). For comparison, a bare gold electrode or gold modified with either 2-ME or 2-ME/mercapto-oligonucleotides lacking ferrocene produces featureless CV curves in the same potential window. The apparent formal potential of the electroactive label is $E^0=0.492$ V, as estimated from $E_{1/2}=(E_{red}+E_{ox})/2$. This value falls within the typical redox potential range of ferrocene ($E^0$ of ferrocene is slightly sensitive to the environment, but remains within a relatively limited potential range) [Brazill, S. A., Kim, P. H. & Kuhr, W. G., *Anal. Chem.* 73, 4882-4890 (2001)]. Therefore, this peak pair was ascribed to the redox conversion of ferrocene labels in close proximity to the gold electrode. It is known that high salt concentration is required for the formation of short stem-loop structures as a result of the electrostatic repulsion between negatively charged DNA chains [Heme, T. M. & Tarlov, M. J., *J. Am. Chem. Soc.* 119, 8916-8920 (1997)]. We found that some freshly modified electrodes do not produce redox peaks without prior incubation in 1 M $NaClO_4$. This result provided strong evidence that the formation of the stem-loop structure facilitated the electron transfer between the gold electrode and ferrocene by constraining the ferrocene label in close proximity to the electrode surface. This result also implied that the use of neutral peptide nucleic acids (PNA) in place of the DNA might provide significant advantages by allowing hybridization to occur at ambient ionic strengths.

Figure 5B:
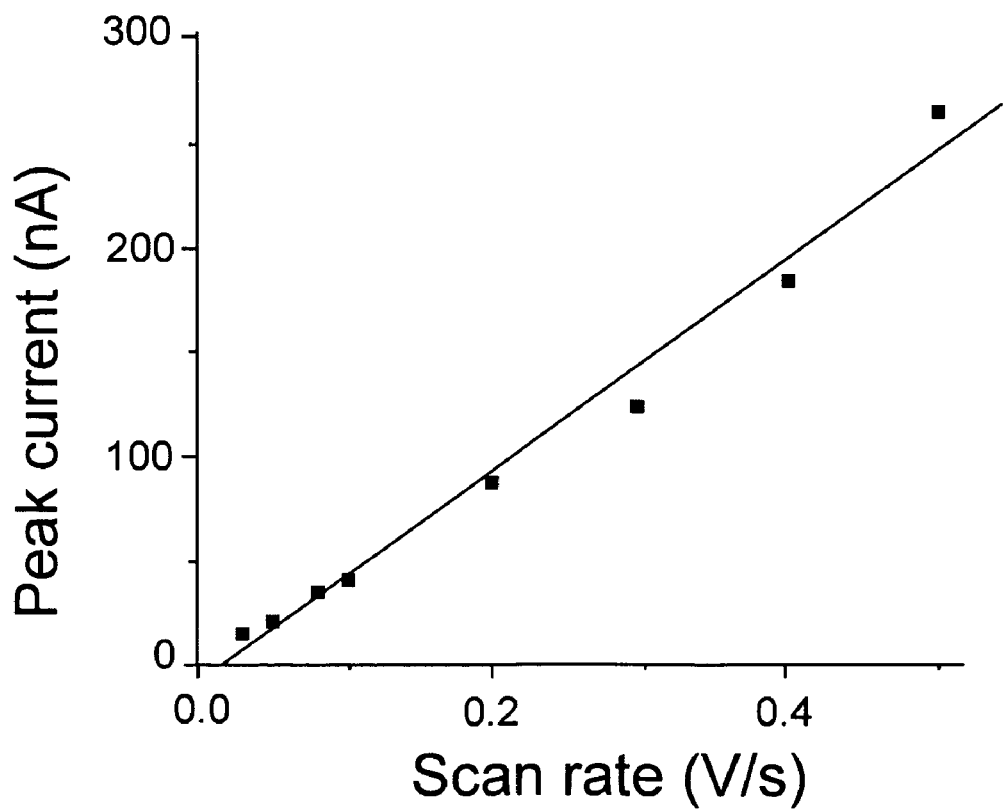
FIG. 5B demonstrates the relationship between the peak current and the scan rate.

Modulating the scan rate of the CVs provided further evidence that ferrocene was confined at the electrode surface by the formation of the stem-loop structure. Peak currents of the ferrocene redox reaction ($I_p$) were directly proportional to scan rates (FIG. 5b), consistent with a surface-confined electrochemical reaction (in contrast to $I_p$ being proportional to the square-root of the scan rate characteristic of diffusion-controlled electrochemical reactions) [Bard, A. J. & Faulkner, L. R. *Electrochemical Methods* (John W. Willey & Sons, New York, 2001)].

Example 4

Target DNA Detection

Figure 7:
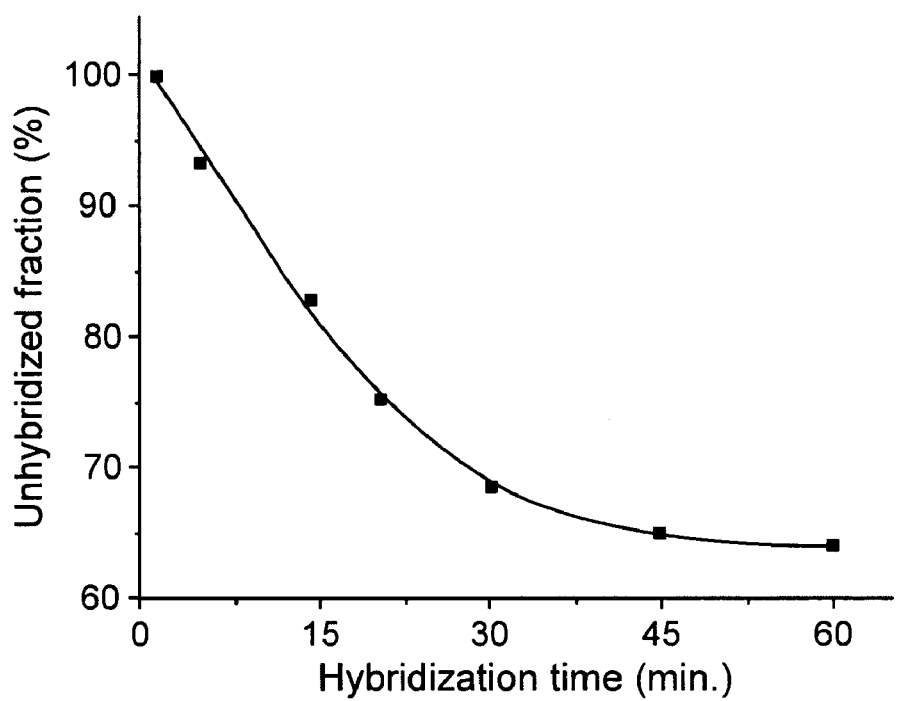
FIG. 7 is a graph illustrating that at a target DNA concentration of 500 pM, the signal develops in minutes. At this target DNA concentration, about 65% of the probe-DNA has been hybridized in one hour (at 5 mM target DNA, the signal goes to zero within 30 minutes).

When the stem-loop structure encounters a sequence complementary to the loop region (17 bases), hybridization disrupts the less stable stem structure and isolates the ferrocene from the electrode surface. Thus, incubating a stem loop-modified electrode in a 5 M cDNA (oligo 2, see Example 1) solution containing 1 M $NaClO_4$ eliminated the ferrocene reduction and oxidation peaks within ~30 min (FIG. 5a). After incubating the electrode with 500 pM cDNA solution and monitoring the hybridization process electrochemically, we observed that the electrochemical signal attenuated with a time constant of approximately 30 min (FIG. 7).

Example 5

Sensor Sensitivity

Employing a fixed 30-minute incubation time, the sensitivity of the sensor was tested. We observed readily measurable decreases in peak intensity at target DNA concentrations as low as 10 pM (FIG. 6). Peak currents were logarithmically related to target concentration across the almost six decade range of sample concentrations we investigated.

Example 6

Sensor Selectivity

Figure 6A:
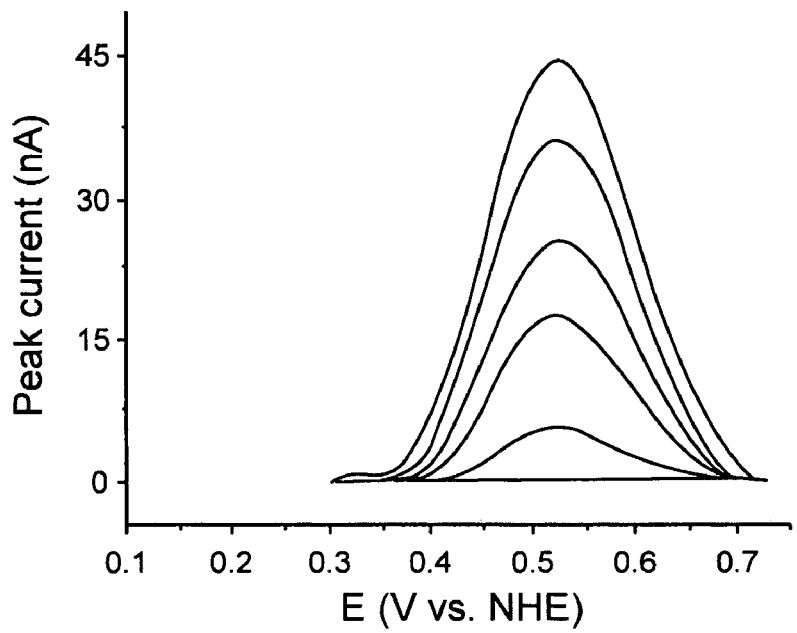
FIG. 6A is a series of background-subtracted [Fan, C., Gillespie, B., Wang, G., Heeger, A. J. and Plaxco, K. W., *J. Phys. Chem.* (B) 106, 11375-11383 (2002); Hirst, J. et al. *J. Am. Chem. Soc.* 120, 7085-7094 (1998)] voltammograms (anodic scan) for a hairpin-forming, DNA-modified gold electrode in the presence of complementary DNA (cDNA) at different concentrations: 0, 30 pM, 500 pM, 30 nM, 800 nM, 5 μM (from bottom to top). The hybridization was performed in a 1 M $NaClO_4$ solution, and the hybridization time was fixed at 30 min.
Figure 6B:
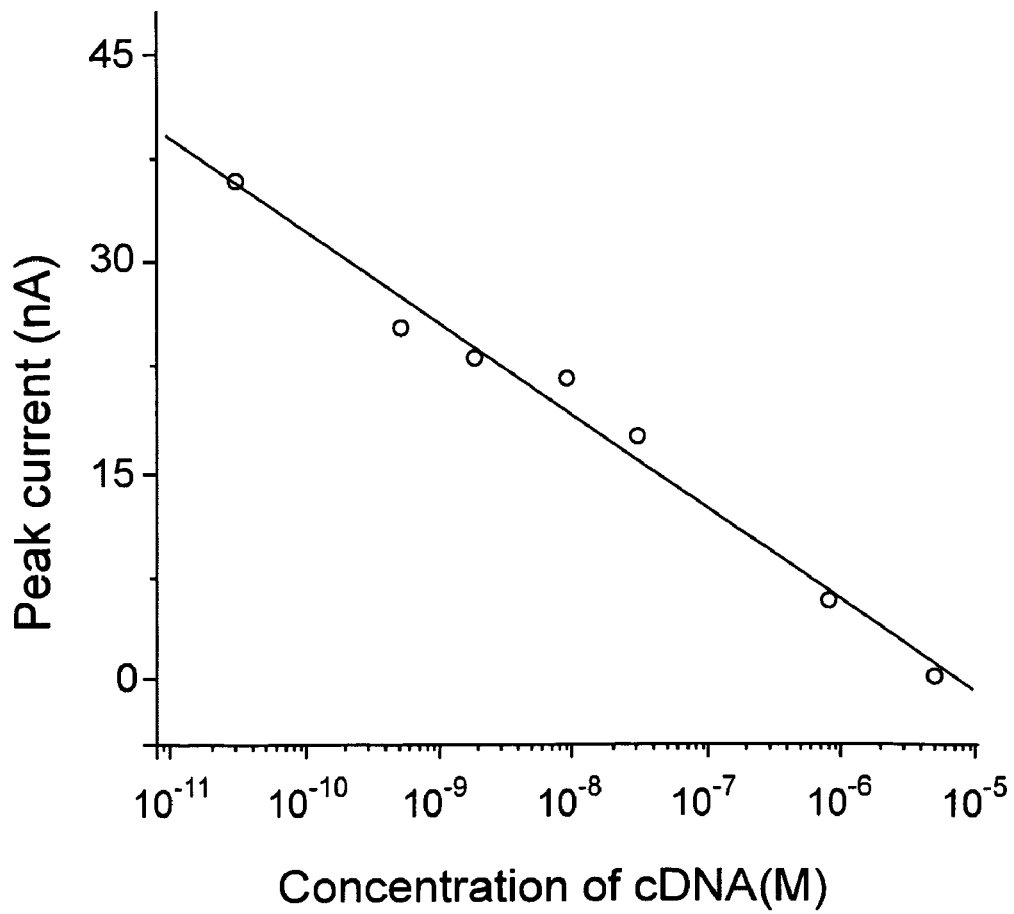
FIG. 6b is a calibration curve (peak height vs. concentration of the cDNA).

The E-DNA sensor was highly selective. Employing a fixed 30-minute incubation time, we tested the sensitivity of the sensor. We observed readily measurable decreases in peak intensity at target DNA concentrations as low as 10 pM (FIG. 6a). Peak currents were logarithmically related to target concentration across the almost five decade range of sample concentrations we investigated (FIG. 6b).

No significant signal change was observed for electrodes incubated in DNA-free hybridization buffer or in the presence of the highest non-target DNA concentrations we investigated (10 M oligo 3, see Example 1). Thus the selectivity of the sensor relative to a random target sequence was in excess of $10^6$.

Example 7

Sensor Regeneration

The electrochemical DNA sensor was readily reusable. Washing the electrode with 1 M $NaClO_4$ at 95° C. and re-challenging with the target sequence, we successfully recovered up to about 80% of the original signal. The minor loss of the signal during recovery presumably resulted from the relative instability of ferrocene at high temperature. Other redox labels are more thermostable.

Example 8

Fabrication of the Stem-Loop DNA Structure with MB Label

Oligonucleotides were obtained from Synthegen (Houston, Tex.). The sensor oligonucleotide, 5'-$NH_2$—$(CH_2)_6$-GC-GAG GTA AAA CGA CGG CCA GT CTCGC-$(CH_2)_6$—SH-3' (SEQ ID NO: 1) (oligo 1), contained a 5' hexamethylene amine and a 3' hexamethylene thiol group. A methylene blue (MB) tag was conjugated to oligo 1 through coupling the succinimide ester of MB (MB-NHS, EMP Biotech, Germany) with the 5' amine of oligo 1. The final product (oligo 1-MB) was purified by HPLC on a C18 column and confirmed by electrospray mass spectroscopy. The sequences of the target and control DNA oligos were 5'-ACTGGC-CGTCGTTTTAC-3' (SEQ ID NO: 4) (oligo 2) and 5'-CG-TATCATTGGACTGGC-3' (SEQ ID NO: 5) (oligo 3), respectively. Oligo 2 is fully complementary to the loop sequence while the control oligo 3 is a sequence unrelated to the probe sequence, which was used as the masking DNA.

Example 9

Preparation of the Functionalized Gold Electrode

Polycrystalline gold disks (1.6 mm diameter) (BAS Inc., West Lafayette, Ind.) were used as working electrodes. The E-DNA sensor was constructed by assembling the MB-labeled DNA stem-loop at the gold electrode. In order to construct the sensor as demonstrated in FIG. 4, a 0.1 mM solution of the stem-loop oligo 1-MB (with 100 mM NaCl, 5 mM $MgCl_2$ and 10 mM phosphate buffer at pH 7.0) was self-assembled on an extensively cleaned gold surface (Leopold, M. C., Black, J. A. and Bowden, E. F., *Langmuir* 18, 978-980 (2002); Fan, C., Gillespie, B., Wang, G., Heeger, A. J. and Plaxco, K. W., *J. Phys. Chem.* (B) 106, 11375-11383 (2002).). The prepared surface was subsequently passivated with excess 6-mercaptohexanol at 1 mM for about 2 hrs. The modified electrode was thoroughly rinsed, dried and then incubated in 1 M NaCl prior to use.

Example 10

Description of the MB Labeled E-DNA Sensor

Cyclic voltammetry (CV) and AC voltammetry (ACV) were performed at room temperature using a CHI 603 workstation (CH Instruments, Austin, Tex.). In ACV, we employ 10 Hz frequency and 25 mV amplitude. Potentials are reported versus the Ag/AgCl, 3 M NaCl reference electrode (BAS Inc.). A platinum wire was used as the counter electrode.

MB, as well as the previously employed ferrocene, is readily redoxable at gold electrodes. As demonstrated in FIG. 8, a pair of well-defined peaks were obtained for E-DNA in the absence of targets, which corresponds to the redox conversion of the MB label in close proximity to the gold electrode. Upon hybridization with complementary sequence to the loop range, the unfolding of the stem-loop moves the MB away from the electrode surface, which significantly decreases the electrochemical signal.

Figure 8:
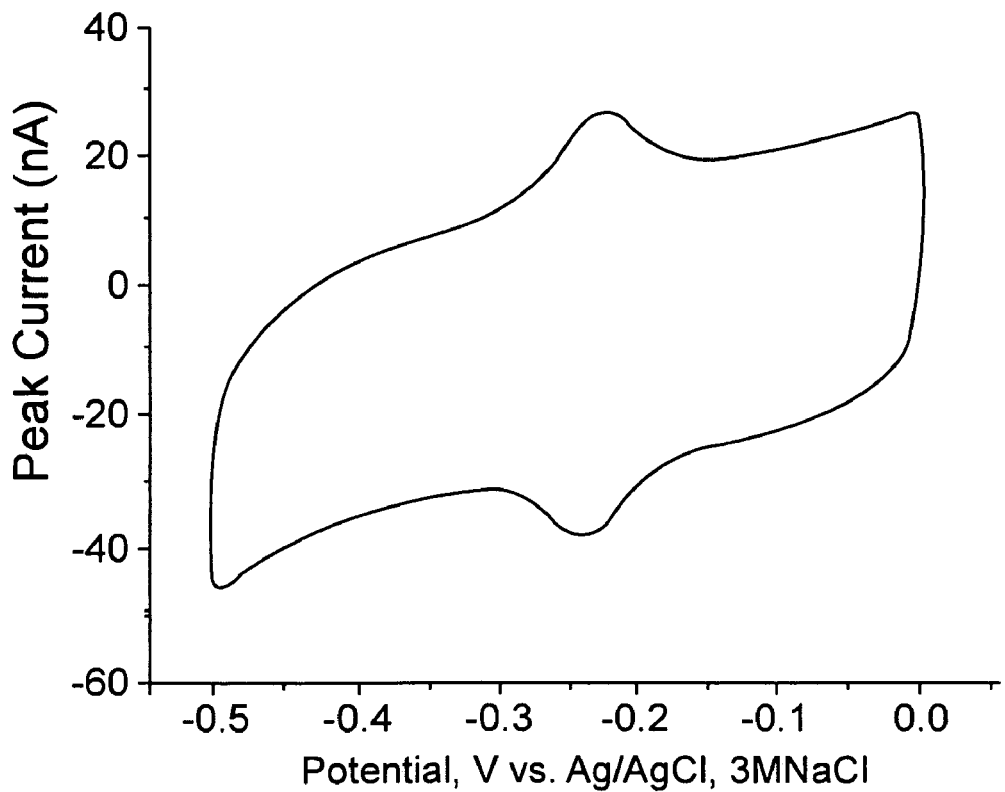
FIG. 8 is a cyclic voltammogram for a gold electrode modified with a methylene blue-tagged oligonucleotide in the absence of target oligonucleotide.

FIG. 8 provides a cyclic voltammogram for a gold electrode modified with the MB tagged, stem-loop oligonucleotide in the absence of target DNA (scan rate of 0.1 V/s). The electrolyte is 10 mM phosphate buffer/1 M NaCl, pH 7.0.

Figure 9:
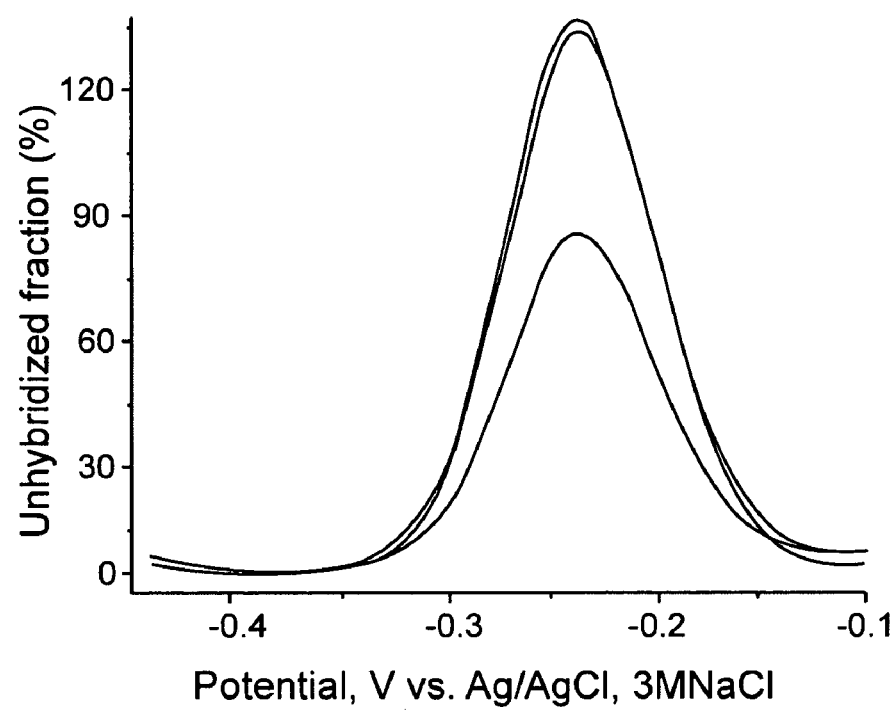
FIG. 9 is a series of AC voltammograms for the E-DNA sensor before a test (upper line) and after a test with DNA microdots containing masking DNA only (lower line) and masking DNA with target DNA (upper line).

The MB-labeled E-DNA sensor works in alternating current voltammetry mode (ACV). ACV typically involves the application of a sinusoidally oscillating voltage to an electrochemical cell which has proven to effectively reduce charging (background) current (O'Connor, S. D., Olsen, G. T. and Creager, S. E. *J. Electroanal. Chem.* 466, 197-202 (1999).). As shown in FIG. 9, the ACV of E-DNA has a nearly flat background, making the comparison between curves both convenient and quantitative. Consequently, ACV was used in the following DNA authentication studies.

FIG. 9 provides AC voltammograms for the E-DNA sensor before the test, and after the test with DNA microdots containing masking DNA (50 mg) only, and masking DNA (50 mg) mixed with target DNA (5 ng). The hybridization time was 30 minutes.

Use of the MB label results in at least three advantages. First, in the ferrocene labeled E-DNA sensor, the electrochemical experiments are best performed only in certain salt solutions (e.g., perchlorate), because ferrocene, if oxidized, is vulnerable to strong nucleophiles (e.g., chlorides) (Han, S. W., Seo, H., Chung, Y. K. & Kim, K., *Langmuir* 16, 9493-9500 (2000)). This limitation has been overcome via the employment of MB label, which is more stable in chloride solutions. Therefore, the use of MB labels not only avoids the risk of using potentially dangerous perchlorates, but avoids the necessity of removing possible chloride contaminations.

Second, ferrocene has little affinity for DNA strands, therefore the labeled ferrocene dangles under the stem-loop which may increase the surface heterogeneity. This effect is reflected by the non-ideal electrochemistry of ferrocene, such as decreased electron transfer rates and broadened peaks, due to dispersion of kinetic and thermodynamic parameters (rate constants, formal potentials etc.) (Saccucci, T. M. & Rusling, J. F. *J. Phys. Chem.* (B) 105, 6142-6147 (2001); Clark, R. A. & Bowden, E. F. *Langmuir* 13, 559-565 (1997)). In contrast, MB, a DNA intercalator, inserts into the stem double helix (Muller, W. and Crothers, D. M., *Eur. J. Biochem.* 54, 267-277 (1975); Boon, E. M., Salas, J. E. & Barton, J. K., *Nat. Biotechnol.* 20, 282-286 (2002)). Intercalation limits diffusion of the label, which leads to much improved electrochemical behavior, including sharper peaks (less thermodynamic dispersion) and smaller peak separations (less kinetic dispersion) (FIG. 1). For example, for CVs at 100 mV/s, the n×FWHM (full width at half-maximum) has been reduced from ~170 mV to ~140 mV, and the n×DE has been reduced from ~60 mV to ~30 mV in the MB labeled E-DNA (n stands for the electron transfer numbers).

Third, MB is very stable against thermal degradation in water and provides a more readily reusable sensor. This means that an MB-based sensor can be washed with hot water to remove hybridized target and give a good strong signal when reused.

Example 11

Document Authentication with E-DNA Sensor

The feasibility of encapsulating DNA sequence information in a piece of filter paper was tested. The E-DNA sensor was used as a convenient readout device. 1 ml of the DNA solution (~5 ng oligo 2 with 10,000-fold excess of non-cognate DNA oligo 3) was added to a small circle (~3 mm diameter) printed on filter paper with a ball pen. Interestingly, the DNA solution was confined in this cycle, possibly due to the fact that the diffusion of the solution in the filter paper was hindered by the hydrophobic pen ink. This DNA microdot, after being dried, was cut from the paper and immersed in 20 ml salt water containing 10 mM phosphate buffer with pH 7.0 and 1 M NaCl for approximately 10 min. 2 ml of the eluted solution was placed at the E-DNA electrode surface. After 30-min hybridization, the ACV signal dropped by about 40%. As a control, the E-DNA signal remain and almost unchanged in the case of a DNA microdot with only 50 mg masking DNA (oligo 3) (FIG. 9 and FIG. 10).

Figure 10:
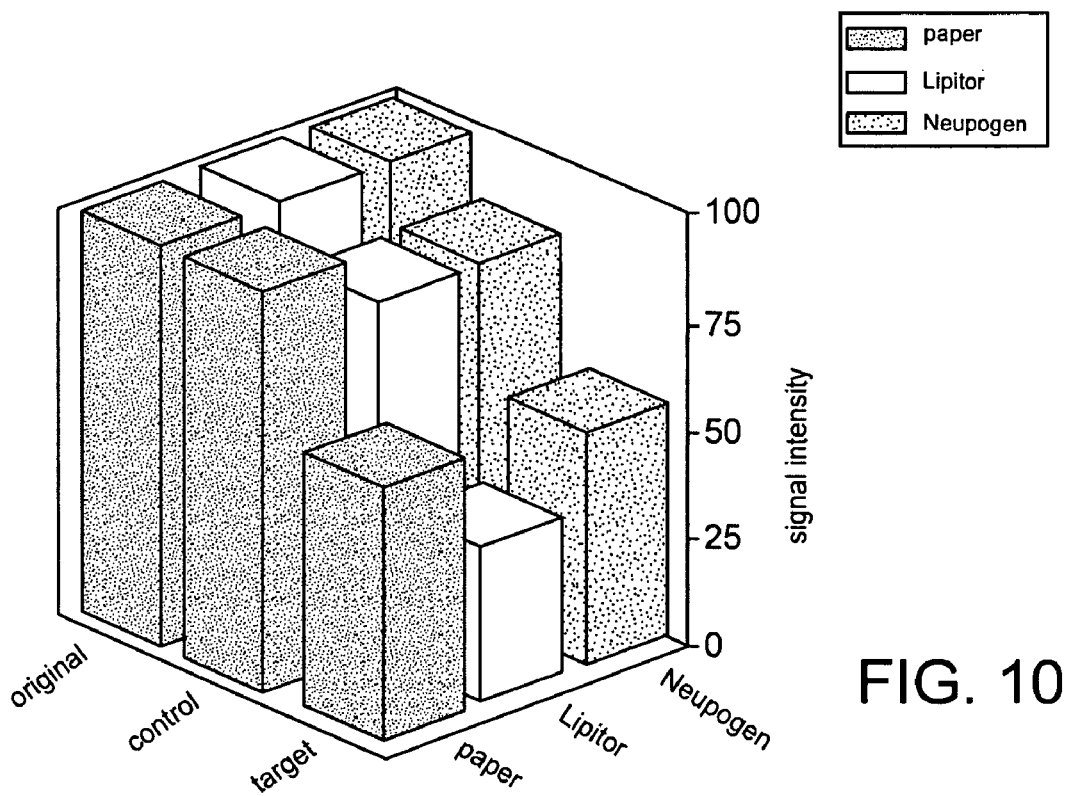
FIG. 10 is a graphic comparison among the E-DNA authentication signals observed before and after counterfeiting tests on three possible counterfeited objects.
Figure 11:
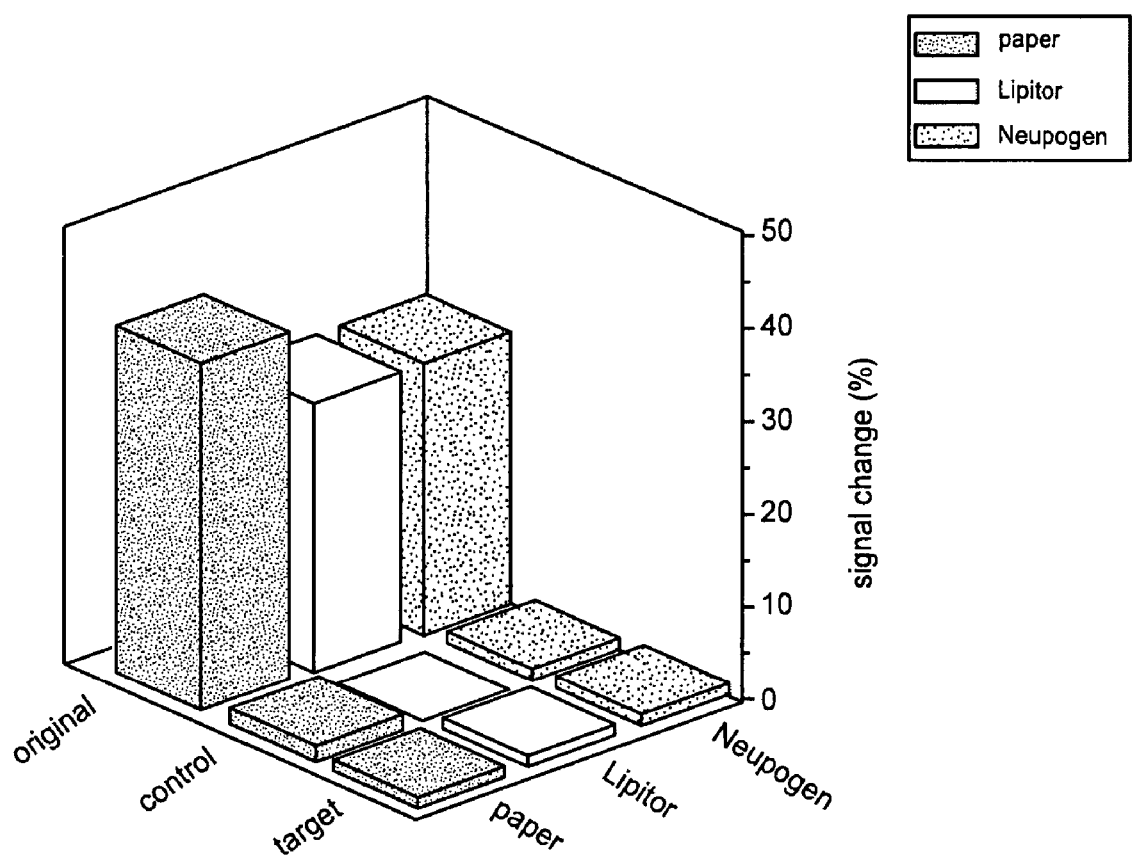
FIG. 11 is a graphic comparison among E-DNA authentication signals generated in essentially the same manner as the signals in FIG. 10 with the addition of glycerol as an additive to reduce background noise. This figure displays the amount of signal change that was observed.

FIG. 10 provides comparisons among the E-DNA signals before and after counterfeiting test in filter paper, LIPITOR® (Atorvastatin Calcium) and NEUPOGEN® (Filgrastim).

This experiment clearly demonstrates the need for a very small amount of DNA oligo (~5 ng), having the target sequence, to "authenticate" the provenance of documents. This sequence information can be read through an E-DNA sensor with the appropriate probe DNA. The extremely high specificity has enabled one to mask the sequence information in 10,000-fold excess of non-cognate "masking" DNA. The use of such a large excess of "masking" DNA will significantly impede counterfeiting efforts based on sequencing or cloning of the DNA authentication tag. Although this preliminary experiment was performed with filter paper, previous studies have proven it possible to encapsulate DNA in other substrates such as typical letter paper, with stability over two years at room temperature. However, in this case, time-consuming gel electrophoresis methods were used to obtain the results (Cook, L. J. & Cox, J. P. L. *Biotechnol. Lett.* 25, 89-94 (2003)). Given the complexity of DNA sequence information (a 17-mer corresponds to ~seventeen billion combinations), convenience of encapsulation, and readout of the described technology, this DNA authentication technology is promising for authentication of important documents.

Example 12

Thwarting Drug Counterfeiting with E-DNA Sensor

LIPITOR® (Atorvastatin Calcium) tablets were selected as an example of orally ingested drugs and NEUPOGEN® (Filgrastim) as an example of injectable drugs. LIPITOR® (Atorvastatin Calcium) is a cholesterol lowering drug (Pfizer), while NEUPOGEN® (Filgrastim) (Amgen) is a cancer-control drug that fights against Neutropenia, a disease characterized by a low white blood cell count.

The LIPITOR® (Atorvastatin Calcium) tablets were ground into powder and a droplet (approximately 1 µl) of DNA (20 ng oligo 2 with 200 mg masking DNA) was added to the powder. After drying in the air, the powder was dispersed in 50 ml salt water followed by filtering to obtain the supernatant. For the NEUPOGEN® (Filgrastim) liquid, 1 ml NEUPOGEN® (Filgrastim) was mixed with 1 µl DNA (20 ng oligo 2 with 200 mg masking DNA), and then diluted into a 50 ml solution; 2 ml of this solution was pipetted on the gold electrode surfaces. The control experiments were performed using only the masking DNA, in the absence of target DNA tag. As demonstrated in FIG. 10, we observed a significant decrease in the ACV signal after 30-min hybridization. In both cases, significantly smaller decreases of the corresponding signals were observed in the control experiments. The decreases in the control experiments possibly arise from the non-specific adsorption of some components of the drugs. It will be appreciated that one might wish to control the reaction time and the concentration of target DNA in order to obtain optimized results in actual sample detection. Nevertheless, due to the significant differences in response between the target DNA-containing experiments and the control experiments, we here demonstrated that it is possible to use the E-DNA sensor to read out the DNA information hidden in drugs.

Example 13

Reducing Background Signals with Additive Addition

The experiments set forth in Example 12 were repeated with one change. Glycerol (5% by volume) was present in the solutions pipetted onto the gold electrodes. The addition of glycerol greatly reduced the background signal in the control samples and resulted in the change in signal shown in FIG. 11. This experiment illustrates that the addition of materials which block nonspecific interactions between masking DNA and the probe produce a clearer and more specific result.

Example 14

Use of Aptamers to Detect Thrombin

Aptamers are DNA or RNA sequences selected in vitro for their ability to bind specific molecular targets. [A. D Ellington, J. W. Szostak, *Nature* 1990, 346, 818-822; C. Tuerk, L. Gold, *Science* 1990, 249, 505-510; M. P. Robertson, G. F. Joyce, *Nature* 1990, 344, 467-470; B. Louis, G. Linda, L. John, V. Eric, T. John, *Nature* 1992, 355, 564-566.] Due to the ease with which novel aptamers can be fashioned, and their generally impressive selectivity and affinity, they are ideal recognition elements for biosensor applications. [S. S. Iqbal, M. W. Mayo, J. G. Bruno, B. V. Bronk, C. A. Batt, J. P. Chambers, *Biosens. Bioelectron.* 2000, 15, 549-578; W. H. Tan, K. M. Wang, T. J. Drake, *Curr. Opin. Chem. Biol.* 2004, 8, 547-553; S. Tombelli, M. Minunni, E. Luzi, M. Mascini, *Anal. Lett.* 2004, 37, 1037-1052; M. Rajendran, A. D. Ellington, *Comb. Chem. High Throughput Screening* 2002, 5, 263-270.] Aptamers have been employed in a wide variety of sensing technologies, [J. W. Li, X. H. Fang, W. H. Tan, *Biochem. Biophys. Res. Commun.* 2002, 292, 31-40; N. Hamaguchi, A. D. Ellington, M. Stanton, *Anal. Biochem.* 2001, 294, 126-131; W. U. Dittmer, A. Reuter, F. C. Simmel, *Angew. Chem. Int. Ed.* 2004, 43, 3550-3553; V. Pavlov, Y. Xiao, B. Shlyahovsky, I. Willner, *J. Am. Chem. Soc.* 2004, 126, 11768-11769; M. Lee, D. Walt, *Anal. Biochem.* 2000, 282, 142-146; H. A. Ho, M. Leclerc, *J. Am. Chem. Soc.* 2004, 126, 1384-1387; M. Minunni, S. Tombelli, A. Gullotto, E. Luzi, M. Mascini, *Biosens. Bioelectron.* 2004, 20, 1149-1156; S. Fukusho, H. Furusawa, Y. Okahata, *Chem. Commun.* 2002,], 88-89; M. Liss, B. Petersen, H. Wolf, E. Prohaska, *Anal. Chem.* 2002, 74, 4488-4495; T. Hianik, V. Ostatna, Z. Zajacova, E. Stoikova, G. Evtugyn, *Bioorg. Med. Chem. Lett.* 2005, 15, 291-295] including a very promising optical approach termed "aptamer beacons". Aptamer beacons employ a large-scale, binding-induced conformational change in order to modulate the emission of a covalently bound fluorophore [M. Rajendran, A. D. Ellington, *Nucleic Acids Res.* 2003, 31, 5700-5713; J. Li, Z. W. Tang, K. M. Wang, W. H. Tan, *Curr. Proteomics,* 2004, 1, 315-324; X. Fang, Y. Mi, J. J. Li, T. Beck, S. Schuster, W. Tan, *Cell Biochem. Biophys.,* 2002, 37, 71-82]. To date aptamer beacons have been reported for such diverse targets as the small molecule cocaine [M. N. Stojanovic, P. de Prada, D. W. Landry, *J. Am. Chem. Soc.* 2001, 123, 4928-4931] and the proteins Tat [R. Yamamoto, T. Baba, P. K. Kumar, *Genes Cells* 2000, 5, 389-396]. Taq DNA polymerase [C. A. Savran, S. M. Knudsen, A. D. Ellington, S. R. Manalis, *Anal. Chem.* 2004, 76, 3194-3198], platelet-derived growth factor [X. H. Fang, A. Sen, M. Vicens, W. H. Tan, *Chem Bio Chem* 2003, 4, 829-834] and thrombin [J. W. Li, X. H. Fang, W. H. Tan, *Biochem. Biophys. Res. Commun.* 2002, 292, 31-40; N. Hamaguchi, A. D. Ellington, M. Stanton, *Anal. Biochem.* 2001, 294, 126-131; W. U. Dittmer, A. Reuter, F. C. Simmel, *Angew. Chem. Int. Ed.* 2004, 43, 3550-3553].

Because beacons are an optical approach, however, they suffer from several potential drawbacks relative to electronic sensing strategies. These include a requirement for generally bulky, expensive, and power-intensive light sources, detectors and monochromaters, a susceptibility to photobleaching, and potential false signals arising from contaminating fluorophores or quenchers [D. D. L. Bowtell, *Nat. Genet.* 1999, 21, 25-32; E. A. Winzeler, M. Schena, R. W. Davis, *Methods. Enzymol.* 1999, 306, 3-18]. In contrast, the impressive miniaturization of modern microelectronics and the relative stability and environmental insensitivity of electroactive labels suggest that electronic sensors might avoid many of these pitfalls [I. Willner, *Science* 2002, 298, 2407-2408. A. J. Bard, L. R. Faulkner, *Electrochemical Method* (Wiley, New York), 2001; S. A. Brazill, P. H. Kim, W. G. Kuhr, *Anal. Chem.* 2001, 73, 4882-4890; T. Hianik, V. Ostatna, Z. Zajacova, *J. Electroanal. Chem.* 2004, 564, 19-24. ]. Previously described electronic, aptamer-based sensors, however, require either the addition of exogenous reagents or are susceptible to interference from contaminants. While the electrochemical detection of an aptamer-thrombin interaction has been reported, the approach requires complex, multi-step pre-processing and the addition of an exogenous redox label [T. Hianik, V. Ostatna, Z. Zajacova, E. Stoikova, G. Evtugyn, *Bioorg. Med. Chem. Lett.* 2005, 15, 291-295].

This Example describes electronic aptamer based (E-AB) sensors of this invention. The sensor, which is directed against the protein thrombin, is sensitive, selective and reusable, and does not require any chemical modification of the analyte. Instead, the sensor was engineered such that signal change (drop) occurs upon a large, binding-induced conformational change in a redox-modified aptamer upon the target binding.

Figure 12:
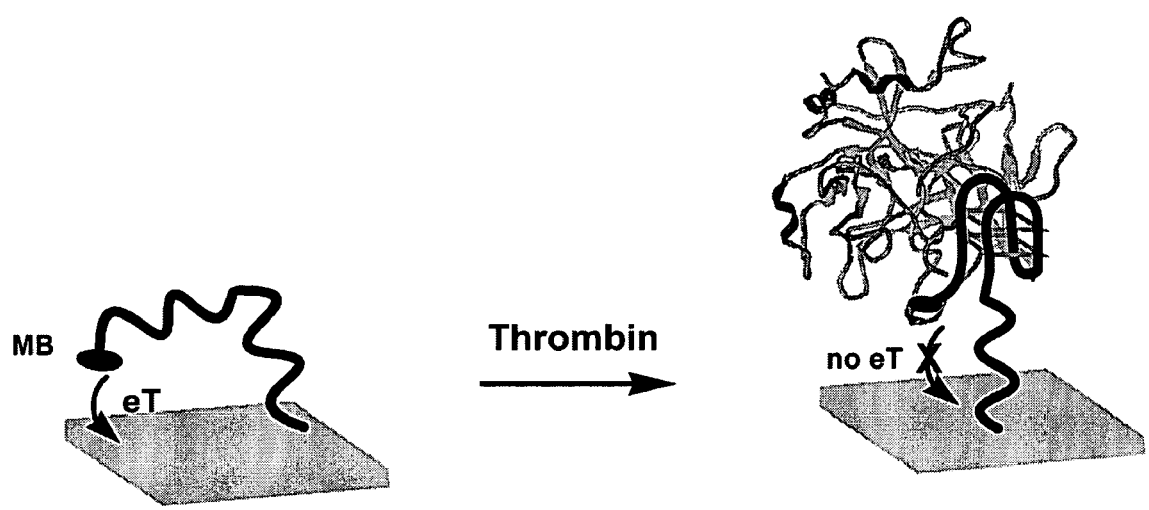
FIG. 12 is a schematic of the electrochemical aptamer-based (E-AB) sensor described in Example 14. In the unbound state (Left), the aptamer is thought to be highly dynamic, allowing for rapid collisions between the methylene blue (MB) redox label and the electrode. This, in turn, presumably allows the efficient electron transfer that is observed in the absence of target. Upon target binding (Right) electron transfer is inhibited, presumably because the aptamer forms a stable, rigid structure.
Figure 13:
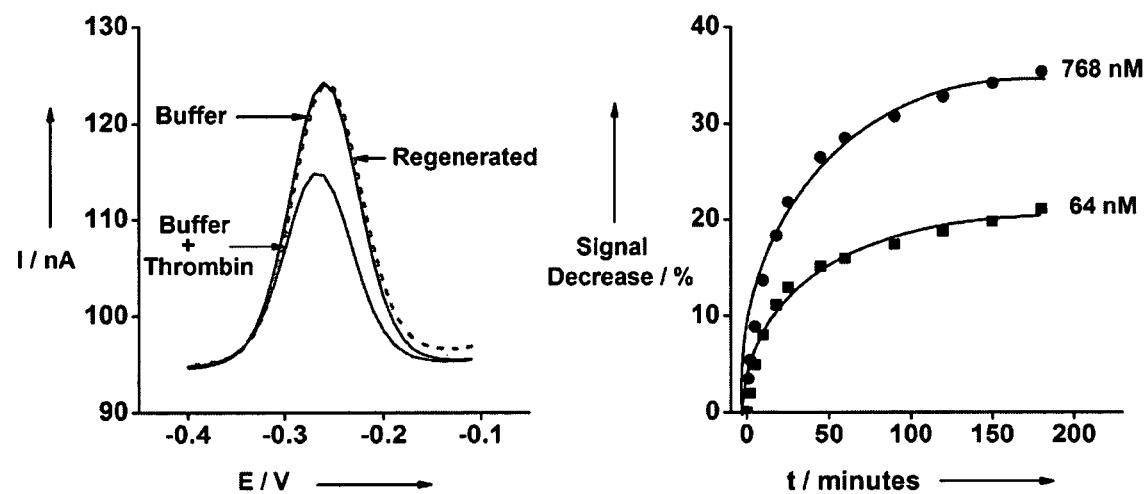
FIG. 13 (Left) is a pair of graphs showing that the E-AB sensor responds robustly to 64 nM thrombin in buffered saline, and can be regenerated via an eight-minute, room temperature wash with guanidine hydrochloride. Even after two cycles of use and regeneration we recover 96% of the original sensor signal (dashed line). (Right) That the sensor response is relatively rapid. While signal saturation is not observed until three hours, the majority of the sensor signal develops in minutes. This is significantly more rapid that traditional, immunochemical methods for protein detection.

The E-AB sensor is constructed by covalently attaching a methylene blue (MB)-labeled, thrombin-binding DNA aptamer (oligo 1) to a gold electrode via well-established self-assembled monolayer chemistry [C. H. Fan, K. W. Plaxco, A. J. Heeger, *Proc. Natl. Acad. Sci. USA* 2003, 100: 9134-9137]. In the absence of target, the immobilized, 32-base aptamer is thought to remain relatively unfolded [J. W. Li, X. H. Fang, W. H. Tan, *Biochem. Biophys. Res. Commun.* 2002, 292, 31-40; N. Hamaguchi, A. D. Ellington, M. Stanton, *Anal. Biochem.* 2001, 294, 126-131; W. U. Dittmer, A. Reuter, F. C. Simmel, *Angew. Chem. Int. Ed.* 2004, 43, 3550-3553]. This presumably allows the attached MB label to collide with the electrode and transfer an electron (FIG. 12, presumed mechanism of the E-AB sensor). Upon thrombin binding the aptamer apparently undergoes a large-scale conformational change [J. W. Li, X. H. Fang, W. H. Tan, *Biochem. Biophys. Res. Commun.* 2002, 292, 31-40; N. Hamaguchi, A. D. Ellington, M. Stanton, *Anal. Biochem.* 2001, 294, 126-131; W. U. Dittmer, A. Reuter, F. C. Simmel, *Angew. Chem. Int. Ed.* 2004, 43, 3550-3553; R. F. Macaya, P. Schltze, F. W. Smith, J. A. Roe, J. Feigon, *Proc. Natl. Acad. Sci. USA* 1993, 90, 3745-3749; R. C. Buijsman, J. W. J. Schipperijn, E. K. Yeheskiely, G. A. van der Marel, C. A. A. van Boeckel, J. H. van Boom, *Bioorg. Med. Chem. Lett.* 1997, 7, 2027-2032], inhibiting electron transfer presumably by altering the electron-tunneling distance and/or pathway (FIG. 13, left). These results also suggest that the immobilized aptamer (oligo 1) is in a conformational equilibrium. Since thrombin should only bind to the G-quartet form [H. A. Ho, M. Leclerc, *J. Am. Chem. Soc.* 2004, 126, 1384-1387], the adding of thrombin promotes the formation of G-quadruplex form of the thrombin aptamer. Because the labeled aptamer is covalently attached to the sensing electrode, the E-AB sensor is readily regenerated: an eight-minute, room-temperature wash with 6 M guanidine hydrochloride is sufficient to regenerate 96% of the original sensor signal (FIG. 13, left). In contrast, several methods previously employed for the regeneration of antibody-based sensors (0.2 M NaOH; 0.25% SDS at pH 10; 6 M urea; 0.2 M HCl, 0.2 M glycine/30% methanol at pH 2; and 10% isopropanol in phosphate buffer, pH 7) produced modest regeneration.

The sensor response is reasonably rapid when compared to other, commonly employed techniques such as ELISAs [J. Bichler, M. Siebeck, R. Maschler, H. Pelzer, H. Fritz, *Blood Coagulation & Fibrinolysis* 1991, 2, 129-133]. While 3 hours incubation is required in order to achieve signal saturation, the majority of the signal change occurs within minutes (FIG. 13, right). Using the Laviron equation [E. Laviron, *J. Electroanal. Chem.* 1979, 101, 19-28] to calculate the interfacial electron transfer rate between the MB and the electrode gives rate-constants of 88 $s^{-1}$ and 58 $s^{-1}$ before and after reacting with thrombin respectively. The similarity in these rates suggests that unbound aptamers produce a similar electron transfer rate irrespective of whether neighboring aptamers are bound to thrombin, and that that upon binding the electron transfer rate becomes undetectably slow.

Figure 14:
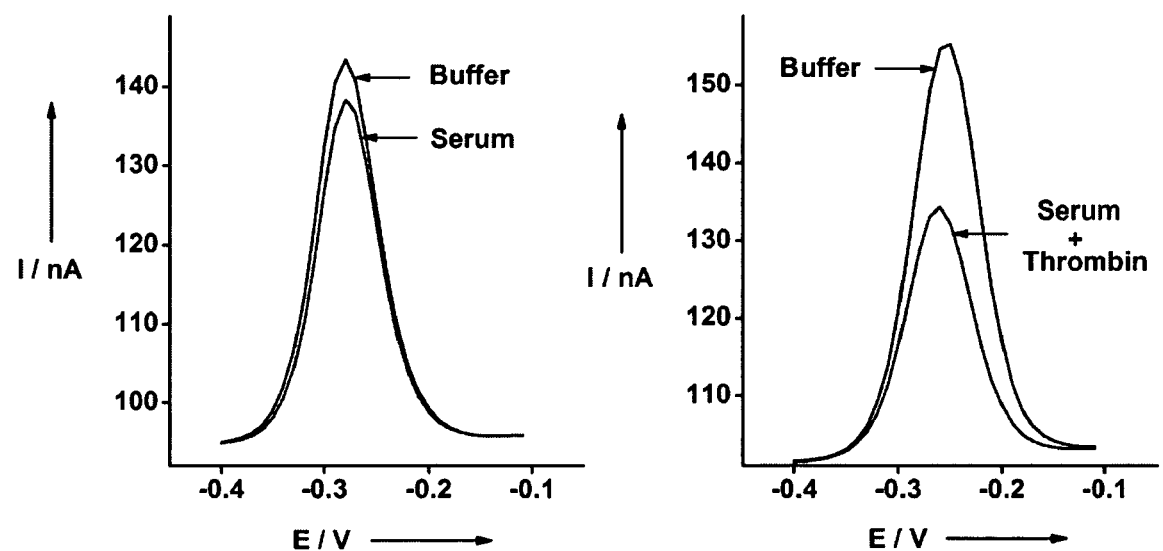
FIG. 14 is a pair of graphs showing that the E-AB sensor can detect thrombin even in a complex, contaminant-ridden sample such as blood serum. Shown is the sensor electrochemical signal arising from thrombin-free buffered saline, from 50% fetal calf serum and from serum doped with 64 nM thrombin.

Because the E-AB signal is based on a specific, binding-induced conformational change [K. Padmanabhan, K. P. Padmanabhan, J. D. Ferrara, J. E. Sadler, A. J. Tulinsky, *Biol. Chem.*, 1993, 268, 17651-17654; I. Smimov, R. H. Shafer, *Biochemistry,* 2000, 39, 1462-1468; B. I. Kankia, L. A. Marky, *J. Am. Chem. Soc.* 2001, 123, 10799-10804]—as opposed to a less-specific physical change such as adsorption—the sensor will be relatively insensitive to non-specific binding. In order to test this, we have found that 64 nM thrombin taken up in blood serum (diluted 50% with buffered saline)—a realistically complex and contaminant-ridden material—produces a large, 35% reduction in peak current (FIG. 14, right). Blood serum lacking exogenously added thrombin, in contrast, produces only a small (~7%) reduction in peak current (FIG. 14, left). The origin of the small signal drop observed in the absence of exogenously added thrombin is unclear. Possible sources include degradation of the aptamer or non-specific interactions mimicking, to a limited extent, the binding-induced sequestration of the MB label. However, neither a MB-labeled stem loop (oligo 2) nor a second, MB-labeled control oligonucleotide (oligo 3) (of identical sequence composition and 81% sequence identity with the DNA aptamer (oligo 1) but known not to bind thrombin[1]) exhibit any measurable signal drop when incubated in serum (data not shown), suggesting that these mechanisms are not significant. In contrast, it is difficult to rule out the possibility that the signal change arises due to the presence of thrombin which, as a blood clotting enzyme, may be present in the undoped serum; while resting (non-clotting) serum thrombin levels are very low, active concentrations soars to several hundred nanomolar during clotting [D. L. Aronson, L. Stevan, A. P. Ball, B. R. Jr. Franza, J. S. Finlayson, *J. Clin. Invest.* 1977, 60, 1410-1418; J. W. Fenton II, *Thrombin: Bioregulartor Functions of Thrombin* (D. A. Walz, J. W. Fenton II, M. A. Shuman, Eds) 1986, *Ann. N. Y. Acad. Sci.*, p5, N.Y. Acad. Sci., New York]. Given that the blood serum employed here is fetal calf serum (a safe proxy for human blood) that was harvested from calves in utero, some activation of the blood-clotting cascade may have occurred, producing detectable levels of thrombin.

Figure 15:
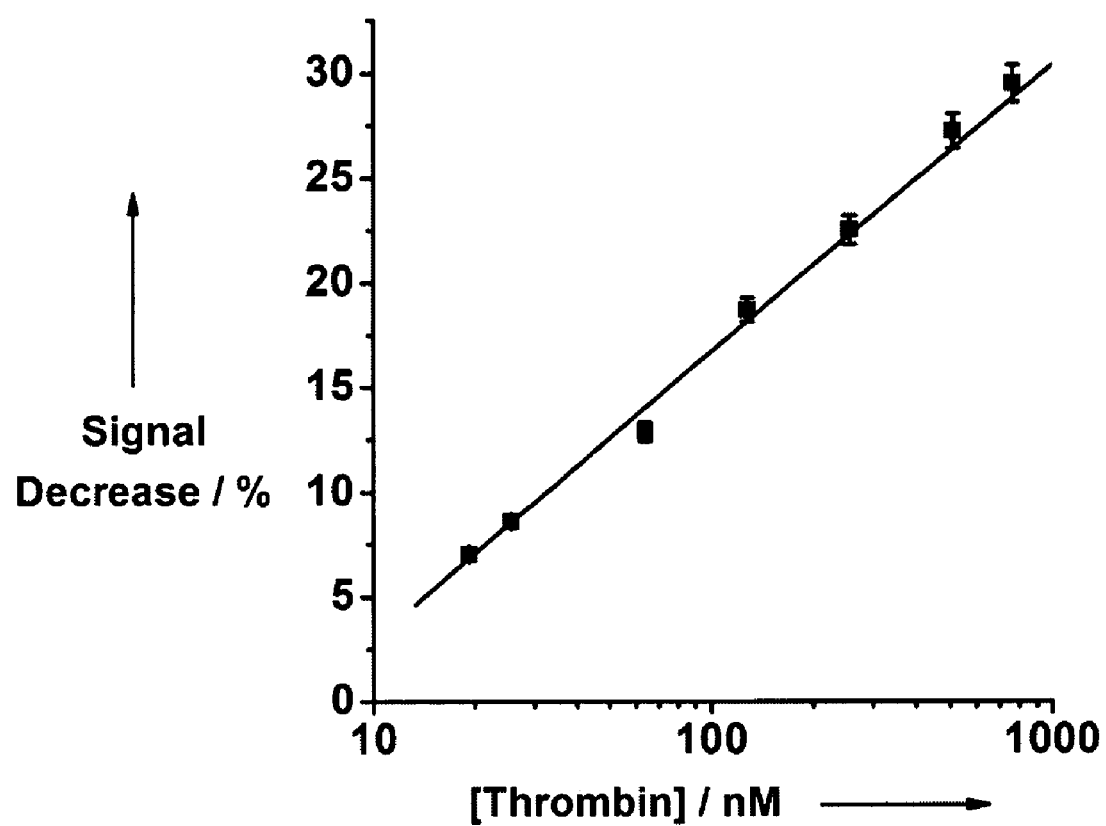
FIG. 15 is a graph illustrating that the dynamic range of the E-AB sensor covers physiologically relevant concentrations, which range from a few nanomolar (resting blood) to several hundred nanomolar when the clotting cascade is activated. The error bars represent the standard deviation of 4 measurements conducted with a single electrode at each thrombin concentration. Multiple electrodes were used to collect the data set.

The sensitivity and dynamic range of the E-AB sensor span the physiological concentrations of thrombin in resting and activated blood, which range from low nanomolar to low micromolar respectively [M. Lee, D. Walt, *Anal. Biochem.* 2000, 282, 142-146]. Except at the very lowest thrombin concentration we have investigated (6.4 nM), peak currents are linear with the logarithm of thrombin concentration (FIG. 15). This linear relationship holds up to the highest thrombin concentrations we have investigated (768 nM). Relative signal changes, however, are dependant on surface coverage; at lower surface coverage than that employed here we observe smaller absolute signals, but higher relative signal change (data not shown). We presume this arises due to reduced steric blocking of unbound aptamers by thrombin binding.

Thus, we have demonstrated a novel, label-free electronic method for the specific and quantitative detection of the blood clotting factor thrombin. The E-AB sensor, which is based on a binding-induced conformational change in a highly selective, high affinity thrombin-binding aptamer, detects the blood protein at nanomolar concentrations without any more cumbersome pre-processing than sample dilution with buffered saline. Moreover, because signal generation does not rely on simple physical adsorption, the sensor is quite insensitive to non-specific binding and thus readily detects physiological thrombin levels even in complex, contaminant-ridden samples such as blood serum. Lastly, the E-AB sensor is reasonably rapid and, given its label-free, fully covalent nature, readily regenerated.

This Example demonstrates a presumably general means by which the binding of such aptamers to their targets can be monitored electronically, thus opening a new direction for the rapid, reusable, sensitive detection of multiple analytes in complex, contaminant-ridden clinical samples.

Labeled DNA oligonucleotides used in this Example were synthesized by BioSource, Int. (Foster City, Calif.), and purified via C18 HPLC and PAGE, and confirmed by mass spectroscopy. The sequences of these three oligomers employed are given below:

(SEQ ID NO: 6)
(1): 5'-HS-(CH$_2$)$_6$-TAAGTTCATCTCCCCGGTTGGTGTGGTTGGT-(CH$_2$)$_2$-MB-3'

(SEQ ID NO: 7)
(2): 5'-HS-(CH$_2$)$_6$-GCGAGGTAAAACGACGGCCAGTCTCGC-(CH$_2$)$_7$-MB-3'

(SEQ ID NO: 8)
(3): 5'-HS-(CH$_2$)$_6$-TAAGTTCATCTCCCCGGTGGTGGTTGTGGTT-(CH$_2$)$_2$-MB-3'

MB was conjugated to the 3' end of these probes via succinimide ester coupling (MB-NHS obtained from EMP Biotech, Germany) [G. T. Hermanson, *Bioconjugate Techniques* (Academic Press, San Diego), 1996]. Inspection of a model of the solution structure of the thrombin-aptamer complex suggests that bases 4 through 12 of the aptamer bind to the anion-binding exosite of thrombin and that the remainder of the aptamer is relatively solvent-exposed [R. F. Macaya, P. Schltze, F. W. Smith, J. A. Roe, J. Feigon, *Proc. Natl. Acad. Sci. USA* 1993, 90, 3745-3749; R. C. Buijsman, J. W. J. Schipperijn, E. K. Yeheskiely, G. A. van der Marel, C. A. A. van Boeckel, J. H. van Boom, *Bioorg. Med. Chem. Lett.* 1997, 7, 2027-2032; K. Y. Wang, S. McCurdy, R. G. Shea, S. Swaminathan, P. H. Bolton, *Biochemistry* 1993, 32, 1899-1904]. This, in turn, suggests that the MB label, which is covalently attached to the 3'-terminal base, should not interfere with thrombin binding.

The human alpha-thrombin used in this study was purchased from Haematologic Technologies Inc. (Essex Junction, Vt., specific activity: 3545 units/mg), and diluted with sterile water as appropriate. Fetal calf serum (FCS) was purchased from Sigma-Aldrich, Inc. (USA) and used without further processing.

The E-AB sensor was fabricated using polycrystalline gold disk electrodes (1.6 mm diameter, BAS, West Lafayette, Ind.). The electrodes were prepared by polishing with diamond and alumina (BAS), sonicating in water, and electrochemically cleaning (a series of oxidation and reduction cycling in 0.5 M NaOH; 0.5 M H$_2$SO$_4$; 0.01 M KCl/0.1 M H$_2$SO$_4$; and 0.05 M H$_2$SO$_4$) before being modified with the probe DNA. The clean gold surface was interacted with a solution of (oligo 1), 0.1 µM including 1 µM TCEP (tris-(2-carboxyethyl)phosphine hydrochloride, which is included to reduce disulfide bonded oligos) in 100 mM Tris buffer, pH 7.4, for 16 hrs. The surface was then rinsed with deionized water and subsequently passivated with 6-mercaptohexanol (1 mM in 10 mM Tris buffer, pH 7.4) for 3 hrs. The electrodes were then rinsed again with 100 mM Tris buffer, pH 7.4, before being measured via alternating current voltammetry (ACV) using a CHI 603 potentiostat (CH Instruments, Austin, Tex.) in a standard cell with a platinum counter electrode and a Ag/AgCl reference electrode. Control electrodes modified with oligonucleotides (2) and (3) were prepared as described for the immobilization of (oligo 1) on gold surface. The surface coverage of the DNA was $1.5\pm0.2\times10^{-12}$ mol/cm$^2$.

Sensor measurements were conducted by monitoring the electrode in 0.1 M Tris, pH 7.4 with 140 mM NaCl, 20 mM MgCl and 20 mM KCl. Neither increasing the final KCl concentration to 150 mM nor changing the pH to 8.5 significantly affected the sensor response (data not shown). Thrombin detection was carried out either in buffered saline (0.1 M Tris, pH 7.4 with 140 mM NaCl, 20 mM MgCl and 20 mM KCl), or fetal calf serum diluted with buffered saline (The serum samples were diluted to 50% with 0.2 M tris, pH 7.4. To 1 mL of this we added 50 □L of saline consisting of 2.94 M NaCl, 0.42 M MgCl$_2$ and 0.42 M KCl.). For all thrombin detection measurements, except the time course study (FIG. 13, right), electrodes were incubated in each sample for 3 hrs at room temperature. E-AB sensors were regenerated by soaking in 6M guanidine-HCl (Pierce, Rockford, Ill.) for 8 min at room temperature, followed by rinsing with deionized water.

Example 15

Use of Aptamers to Detect Cocaine

The experiments of Example 14 were repeated using cocaine as the target and a known aptamer for cocaine, labeled with methylene blue, as the detector probe.

Figure 16:
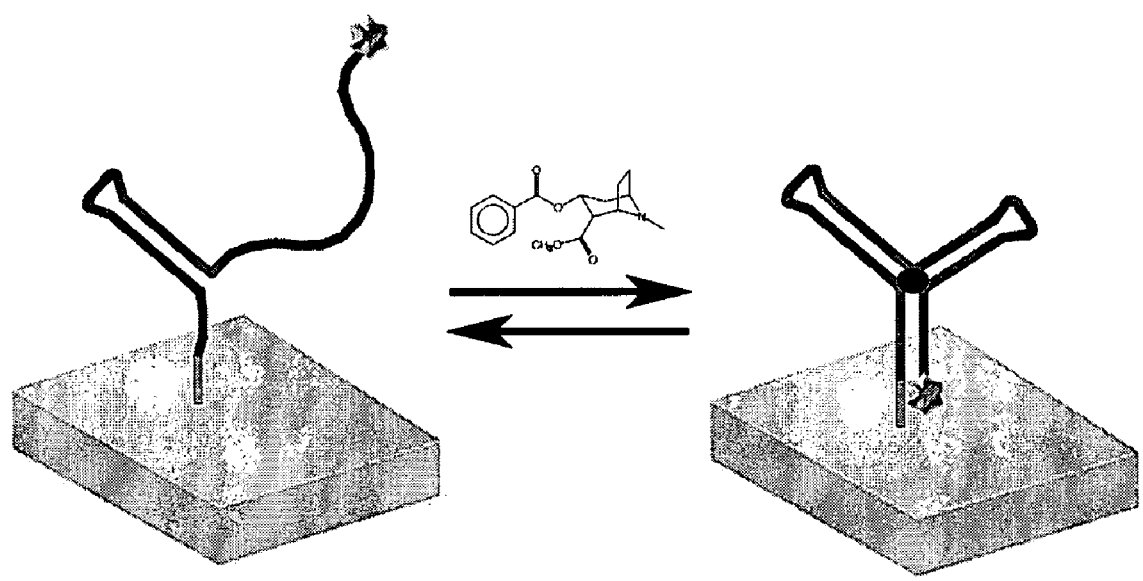
FIG. 16 is a schematic of the electronic aptamer-based (EAB) cocaine biosensor of Example 15 which is fabricated by self-assembly of the methylene blue-labeled aptamer, on gold electrode surface through a six-carbon alkane thiol group at the 5' terminus. In the absence of cocaine target, the aptamer is presumed to remain partially unfolded, with only one of the three stems intact. The 3' terminus, labeled with methylene blue, freely oscillates and periodically approaches the gold surface. In the presence of target, the aptamer apparently folds into a three-way junction, forcing methylene blue close to the electrode surface and thereby facilitating electron transfer and enhancing the observed methylene blue reduction peak.

As shown in FIG. 16 the electronic aptamer-based (EAB) cocaine biosensor of Example 15 which is fabricated by self-assembly of the methylene blue-labeled aptamer, on gold electrode surface through a six-carbon alkane thiol group at the 5' terminus. In the absence of cocaine target, the aptamer is presumed to remain partially unfolded, with only one of the three stems intact. The 3' terminus, labeled with methylene blue, freely oscillates and periodically approaches the gold surface. In the presence of target, the aptamer apparently folds into a three-way junction, forcing methylene blue close to the electrode surface and thereby facilitating electron transfer and enhancing the observed methylene blue reduction peak.

Figure 17:
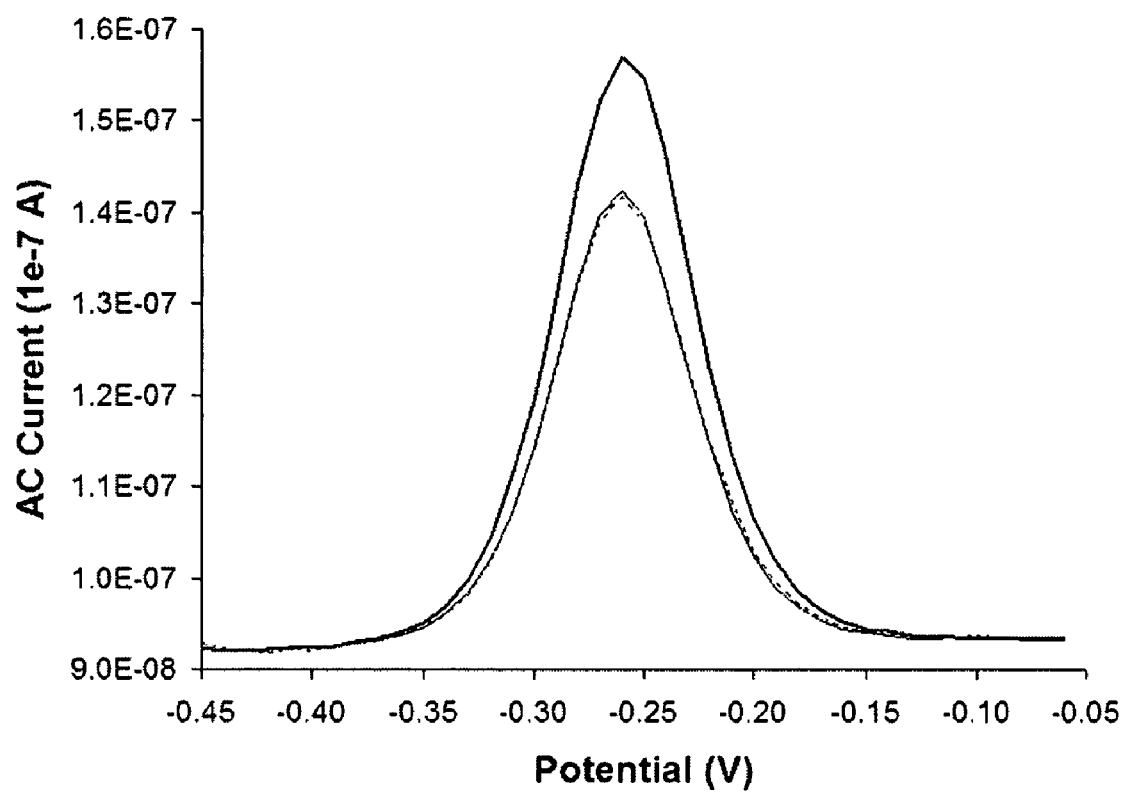
FIG. 17 is a pair of alternating current voltammograms of the cocaine EAB sensor of Example 15 (methylene blue reduction peak) were recorded in 1 M sodium chloride, 10 mM potassium phosphate, pH 7 buffer (dotted line). Upon addition of cocaine stock solution to achieve a 500 μM cocaine concentration, a signal increase was observed (bold line). The sensor was regenerated by simply replacing the cocaine solution with new buffer for three minutes, then replacing again with new buffer for three minutes (solid line).

As shown in FIG. 17 alternating current voltammograms of the cocaine EAB sensor of Example 15 (methylene blue reduction peak) were recorded in 1 M sodium chloride, 10 mM potassium phosphate, pH 7 buffer (dotted line). Upon addition of cocaine stock solution to achieve a 500 µM cocaine concentration, a signal increase was observed (bold line). The sensor was regenerated by simply replacing the cocaine solution with new buffer for three minutes, then replacing again with new buffer for three minutes (solid line).

Figure 18:
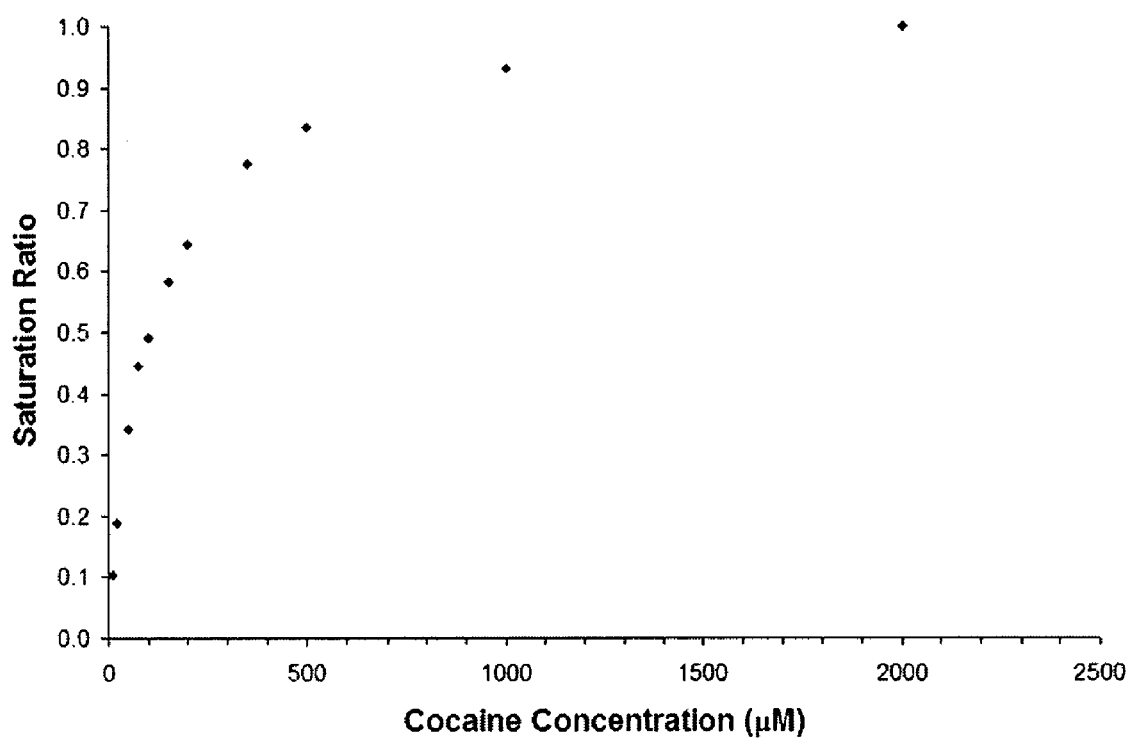
FIG. 18 is a graph of the response of the EAB cocaine sensor of Example 15, immersed in 1 M sodium chloride, 10 mM potassium phosphate, pH 7 buffer, when titrated with cocaine in situ. The sensor displays hyperbolic binding behavior, with a $K_d$ of approximately 90 μM.

As shown in FIG. 18 the response of the EAB cocaine sensor of Example 15, immersed in 1 M sodium chloride, 10 mM potassium phosphate, pH 7 buffer, when titrated with cocaine in situ. The sensor displays hyperbolic binding behavior, with a $K_d$ of approximately 90 µM.

Other test results are provided in the following Table.

TABLE 1

Cocaine samples, mixed with various cutting and masking substances, are subjected to the Scott test (cobaltous thiocyanate) and the cocaine EAB sensor. All samples show a positive test in the cocaine EAB sensor test.

| Sample | Scott Test | Cocaine EAB Sensor |
|---|---|---|
| 500 μM cocaine | Positive | +35% |
| 500 μM cocaine + equal mass flour | . . . | . . . |
| 500 μM cocaine + equal mass sugar | . . . | . . . |
| 500 μM cocaine + 10x mass cobalt(II) thiocyanate | . . . | . . . |
| . . . | . . . | . . . |

What is claimed is:

1. A detector for determining the presence of a target, said detector comprising:
    an electrode capable of sensing redox events in a redox moiety, and
    an oligonucleotide probe immobilized on the electrode, wherein the oligonucleotide probe comprises a redox moiety and a probe nucleotide sequence which specifically interacts with the target when present, and
    wherein, in the absence of specific interaction between the target and the oligonucleotide probe, the redox moiety is located in a first position relative to the electrode, and
    wherein, in the presence of specific interaction between the target and the oligonucleotide probe, said redox moiety is located in a second position relative to the electrode, said first and second positions giving rise to distinguishable redox events detectable by the electrode, wherein the second position results from a disruption of internal hybridization in the probe as a result of the specific interaction between a region in the probe and the target, and wherein the second position is closer to the electrode than the first position.

2. The detector of claim 1, wherein the probe is immobilized on the electrode at a position on the probe distant from the redox moiety.

3. The detector of claim 1, wherein the electrode is capable of inducing redox events in the redox moiety.

4. The detector of claim 1, wherein the second position results from a probe configuration including a loop comprising a region of the target and a region of the probe.

5. The detector of claim 1, wherein the electrode comprises a metal.

6. The detector of claim 5, wherein the metal is gold.

7. The detector of claim 1, wherein the redox moiety is selected from viologen, anthraquinone, ethidium bromide, daunomycin, methylene blue, organo-metallic redox labels, ferrocene, ruthenium, bis-pyridine, tris-pyridine, bis-imidizole, cytochrome c, plastocyanin, and cytochrome c'.

8. The detector of claim 1, wherein said oligonucleotide probe is other than an RNA oligonucleotide probe.

9. The detector of claim 1, wherein said target is an oligonucleotide target and the specific interaction is hybridization.

10. A detector for determining the presence of a target, said detector comprising:
    an electrode capable of sensing redox events in a redox moiety, and
    an oligonucleotide probe, comprising a first region, a second region, and a third region,
    the first region being immobilized upon or proximate to the electrode,
    the third region being bound to a redox moiety,
    the second region being present in the probe intermediate the first and third regions and comprising a first nucleotide sequence which is complementary to and spaced apart from a second nucleotide sequence with which it self hybridizes to form a first loop which positions the redox moiety a first distance from the electrode,
    said first nucleotide sequence also specifically interacting with the target when present, such interacting with the target disrupting the first loop and permitting complementary nucleotide sequences in the second region to self hybridize to form a second loop which positions the redox moiety a second distance from the electrode,
    said first and second distances giving rise to distinguishable redox events detectable by the electrode, wherein, relative to the first distance, the second distance promotes electron transduction between the redox moiety and the electrode.

11. The detector of claim 10 additionally comprising a detector for detecting electron transduction between the electrode and the redox moiety when the second loop is formed.

12. The detector of claim 10 additionally comprising an indicator for inducing electron transduction between the electrode and the redox moiety when the second loop is formed.

13. The detector of claim 10 wherein the first region is at one end of the probe.

14. The detector of claim 10 wherein the third region is at the second end of the probe.

15. The detector of claim 10 wherein the electrode comprises a metal.

16. The detector of claim 15 wherein the metal is gold.

17. The detector of claim 10 wherein the redox moiety is selected from viologen, anthraquinone, ethidium bromide, daunomycin, methylene blue, organo-metallic redox labels ferrocene, ruthenium, bis-pyridine, tris-pyridine, bis-imidizole, cytochrome c, plastocyanin, or cytochrome'.

18. The detector of claim 10, wherein said oligonucleotide probe is other than an RNA oligonucleotide probe.

19. The detector of claim 10, wherein said target is an oligonucleotide target and the specific interaction is hybridization.

20. A method for detecting the presence of a target in a sample, said method comprising:
    contacting the sample under specific interaction conditions with the detector of claim 1; and
    sensing redox events in the redox moiety with the electrode in the presence of the sample and in the absence of the sample, wherein a change in redox events in the presence of the sample relative to the absence of the sample indicates presence of the target in the sample.

21. The method of claim 20, wherein said oligonucleotide probe is other than an RNA oligonucleotide probe.

22. The method of claim 20, wherein said target is an oligonucleotide target and the specific interaction is hybridization.

23. A method for detecting the presence of a target in a sample, said method comprising:
    contacting the sample under specific interaction conditions with the detector of claim 1;
    sensing a redox event in the redox moiety with the electrode; and
    correlating the sensed redox event with at least one redox event sensed in the presence and/or the absence of the target.

24. The method of claim 23, wherein said oligonucleotide probe is other than an RNA oligonucleotide probe.

25. The method of claim 23, wherein said target is an oligonucleotide target and the specific interaction is hybridization.

26. A method for detecting the presence of a target in a sample, said method comprising:
    contacting the sample under oligonucleotide hybridization conditions with the detector of claim 10; and
    sensing redox events in the redox moiety with the electrode in the presence of the sample and in the absence of the sample, wherein a change in redox events in the presence of the sample relative to the absence of the sample indicates presence of the target.

27. The method of claim 26, wherein said oligonucleotide probe is other than an RNA oligonucleotide probe.

28. The method of claim 26, wherein said target is an oligonucleotide target and the specific interaction is hybridization.

29. A method for detecting the presence of a target in a sample, said method comprising:
  contacting the sample under specific interaction conditions with the detector of claim 10;
  sensing a redox event in the redox moiety with the electrode; and
  correlating the sensed redox event with at least one redox event sensed in the presence and/or the absence of the target.

30. The method of claim 29, wherein said oligonucleotide probe is other than an RNA oligonucleotide probe.

31. The method of claim 29, wherein said target is an oligonucleotide target and the specific interaction is hybridization.

32. A method for authenticating an object comprising:
  associating the object with a target; and
  sensing the presence of the target associated with the object using the detector of claim 1, wherein the presence the target indicates that the object is authentic.

33. The method of claim 32, wherein the sensing is carried out in the presence of masking oligonucleotides.

34. A method for authenticating an object comprising:
  associating the object with a target; and
  sensing the presence of the target associated with the object using the detector of claim 10, wherein the presence the target indicates that the object is authentic.

35. The method of claim 34, wherein the sensing is carried out in the presence of masking oligonucleotides.

36. The detector of claim 1, wherein the oligonucleotide probe is a DNA oligonucleotide probe.

37. The detector of claim 36, wherein the oligonucleotide probe is a synthetic DNA oligonucleotide probe.

38. The detector of claim 1, wherein the oligonucleotide probe is a PNA oligonucleotide probe.

39. The detector of claim 10, wherein the oligonucleotide probe is a DNA oligonucleotide probe.

40. The detector of claim 39, wherein the oligonucleotide probe is a synthetic DNA oligonucleotide probe.

41. The detector of claim 10, wherein the oligonucleotide probe is a PNA oligonucleotide probe.

42. The detector of claim 1, wherein the oligonucleotide probe is an aptamer.

43. The detector of claim 10, wherein the oligonucleotide probe is an aptamer.

44. The method of claim 20, wherein the oligonucleotide probe is an aptamer.

45. The method of claim 26, wherein the oligonucleotide probe is an aptamer.

46. The detector of claim 1, wherein in the absence of specific interaction between the target and the oligonucleotide probe, the oligonucleotide probe is present in a first loop configuration, and wherein, in the presence of specific interaction between the target and the oligonucleotide probe, the oligonucleotide probe is present in a second loop configuration.

* * * * *